United States Patent
Chow

(10) Patent No.: US 11,331,204 B2
(45) Date of Patent: May 17, 2022

(54) METHODS AND TOOLS FOR HIP REPLACEMENT WITH SUPERSCAPSULAR PERCUTANEOUSLY ASSISTED TOTAL HIP APPROACH

(71) Applicant: MicroPort Orthopedics Holdings Inc., Arlington, TN (US)

(72) Inventor: James Chow, Paradise Valley, AZ (US)

(73) Assignee: MicroPort Orthopedics Holdings Inc., Arlington, TN (US)

( * ) Notice: Subject to any disclaimer, the term of this patent is extended or adjusted under 35 U.S.C. 154(b) by 0 days.

(21) Appl. No.: 17/143,591

(22) Filed: Jan. 7, 2021

(65) Prior Publication Data
US 2021/0121303 A1 Apr. 29, 2021

Related U.S. Application Data

(63) Continuation of application No. 16/686,512, filed on Nov. 18, 2019, which is a continuation of application
(Continued)

(51) Int. Cl.
*A61F 2/46* (2006.01)
*A61B 17/16* (2006.01)
(Continued)

(52) U.S. Cl.
CPC ............ *A61F 2/4637* (2013.01); *A61B 17/02* (2013.01); *A61B 17/0218* (2013.01); *A61B 17/1666* (2013.01); *A61B 17/1668* (2013.01); *A61B 17/1728* (2013.01); *A61B 17/1746* (2013.01); *A61B 17/1753* (2013.01); *A61B 17/848* (2013.01); *A61B 17/8866* (2013.01); *A61B 90/06* (2016.02); *A61F 2/4603* (2013.01); *A61F 2/4607* (2013.01); *A61F 2/4609* (2013.01); *A61F 2/4657* (2013.01);
(Continued)

(58) Field of Classification Search
CPC ...... A61F 2002/4641; A61F 2002/4619; A61F 2/4637; A61F 2/4603; A61F 2/4607; A61F 2/4609; A61F 2/4612; A61B 17/66; A61B 17/0218; A61B 17/8866; A61B 17/02; A61B 17/92; A61B 17/025; A61B 2017/681; A61B 2017/0275
See application file for complete search history.

(56) References Cited

U.S. PATENT DOCUMENTS

| 5,431,153 | A | * | 7/1995 | Lee | A61B 17/0218 600/183 |
| 2005/0228233 | A1 | * | 10/2005 | Ritland | A61B 17/025 600/210 |
| 2013/0211201 | A1 | * | 8/2013 | Wongsiri | A61B 90/30 600/202 |

* cited by examiner

*Primary Examiner* — Amy R Sipp
(74) *Attorney, Agent, or Firm* — Robert J. Hornung

(57) ABSTRACT

A minimally invasive surgical procedure for replacing a hip joint is provided. A main incision is initiated at a point being a projection of a tip of a greater trochanter and extends proximally about a distance in the range of from 1 cm to 8 cm in line with the femoral axis. An inline capsulotomy is performed, while keeping muscles and posterior capsule intact, to expose the hip joint capsule for accessing the hip joint. The femoral canal is prepared for receipt of a femoral implant. The femoral head is resected and removed out of the acetabulum. A step of acetabular preparation is performed using a retractor comprising two tip rails, each tip rail having a plurality of tines. Related tools, devices, systems and methods are also provided.

8 Claims, 44 Drawing Sheets

Related U.S. Application Data

No. 14/910,632, filed as application No. PCT/IB2014/002418 on Aug. 6, 2014, now Pat. No. 10,478,317.

(60) Provisional application No. 61/862,865, filed on Aug. 6, 2013.

(51) Int. Cl.
| | |
|---|---|
| *A61B 17/88* | (2006.01) |
| *A61B 17/84* | (2006.01) |
| *A61B 17/02* | (2006.01) |
| *A61B 90/00* | (2016.01) |
| *A61B 17/17* | (2006.01) |
| *B65D 81/34* | (2006.01) |
| *A61B 17/00* | (2006.01) |
| *A61B 17/14* | (2006.01) |
| *A61B 17/56* | (2006.01) |

(52) U.S. Cl.
CPC ........ *B65D 81/3453* (2013.01); *A61B 17/142* (2016.11); *A61B 17/1604* (2013.01); *A61B 17/1796* (2013.01); *A61B 2017/0046* (2013.01); *A61B 2017/0275* (2013.01); *A61B 2017/561* (2013.01); *A61B 2090/062* (2016.02); *A61F 2/4684* (2013.01); *A61F 2002/4641* (2013.01); *A61F 2002/4662* (2013.01)

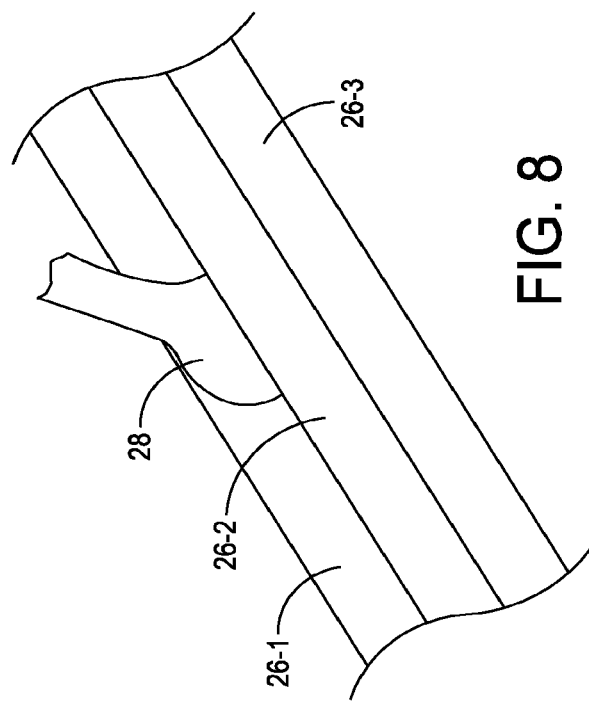
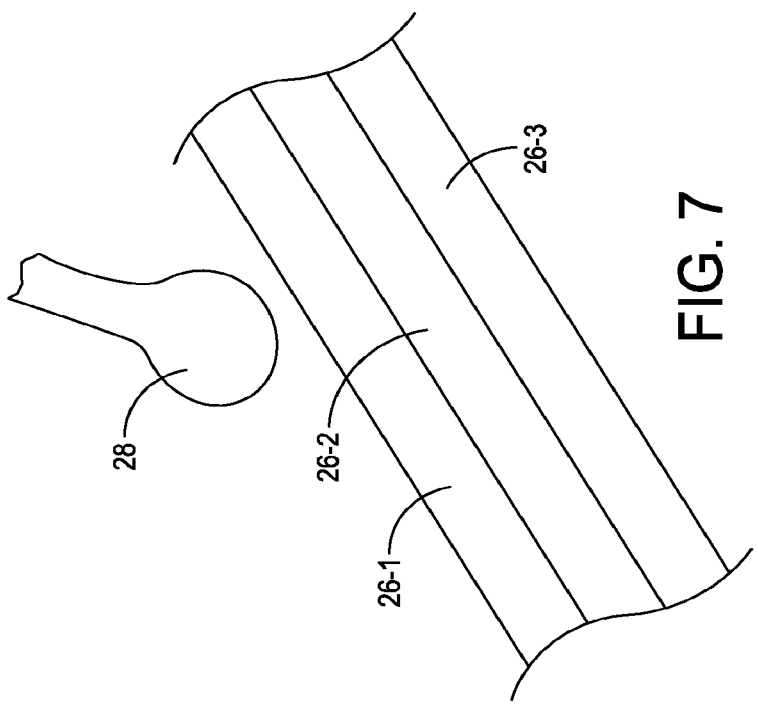

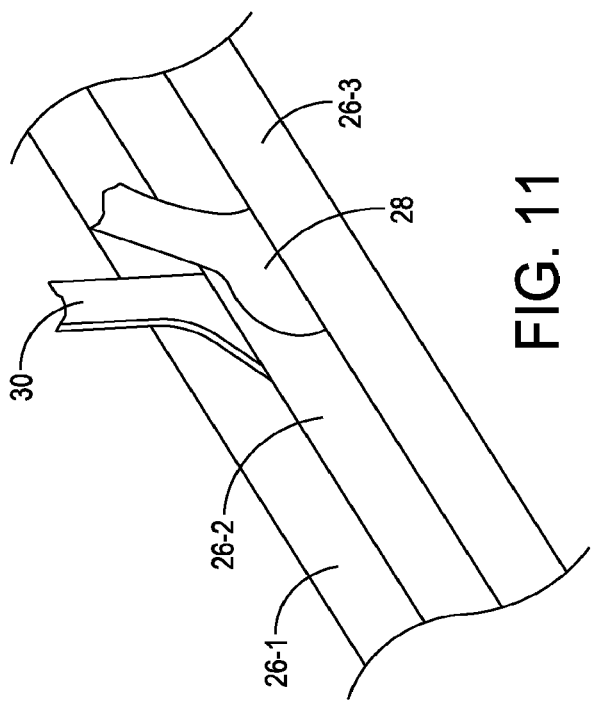
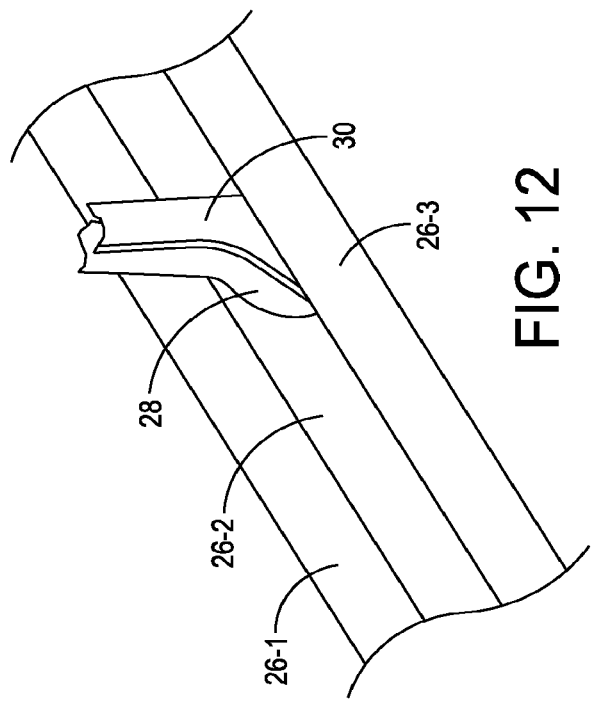

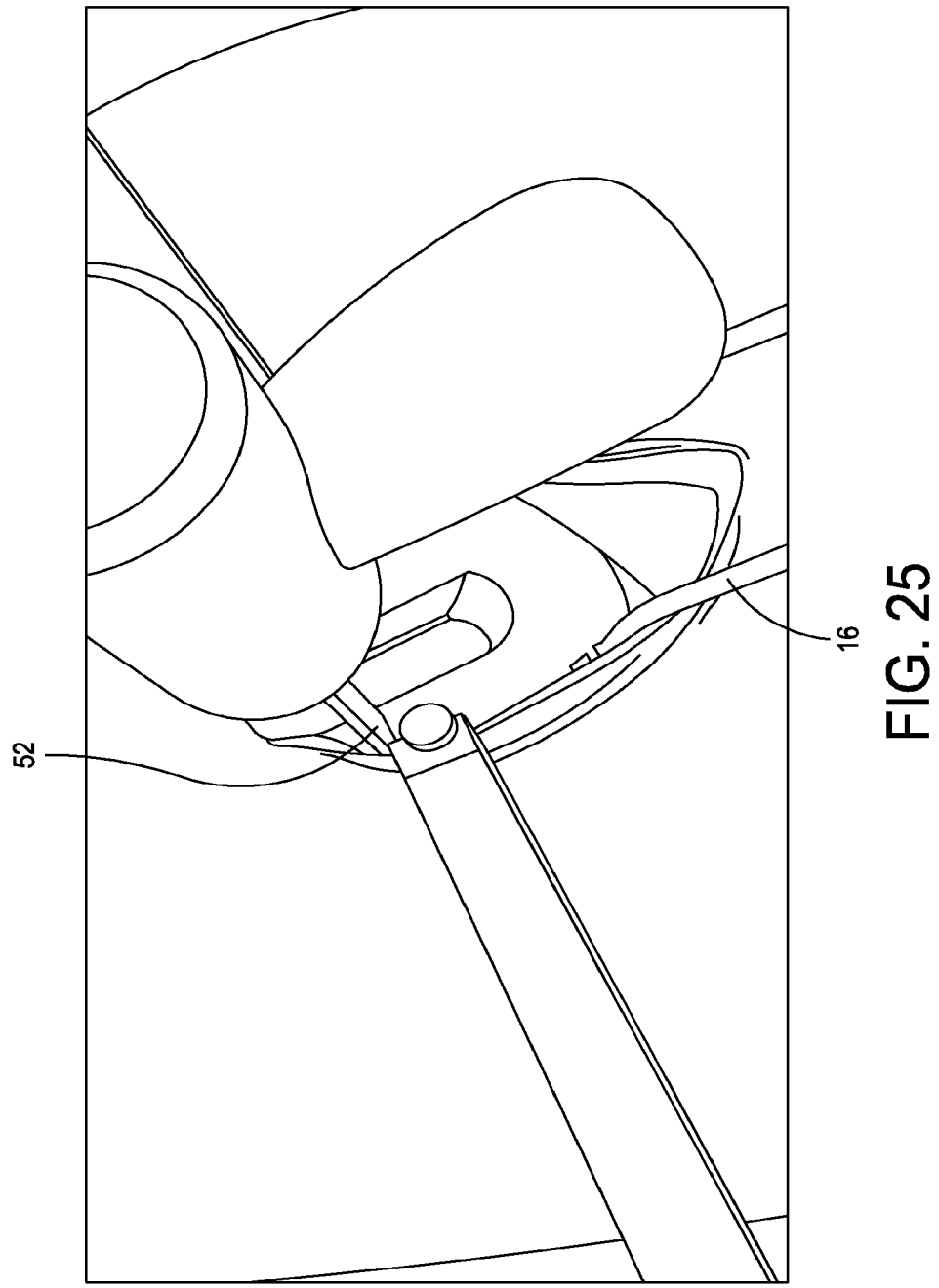

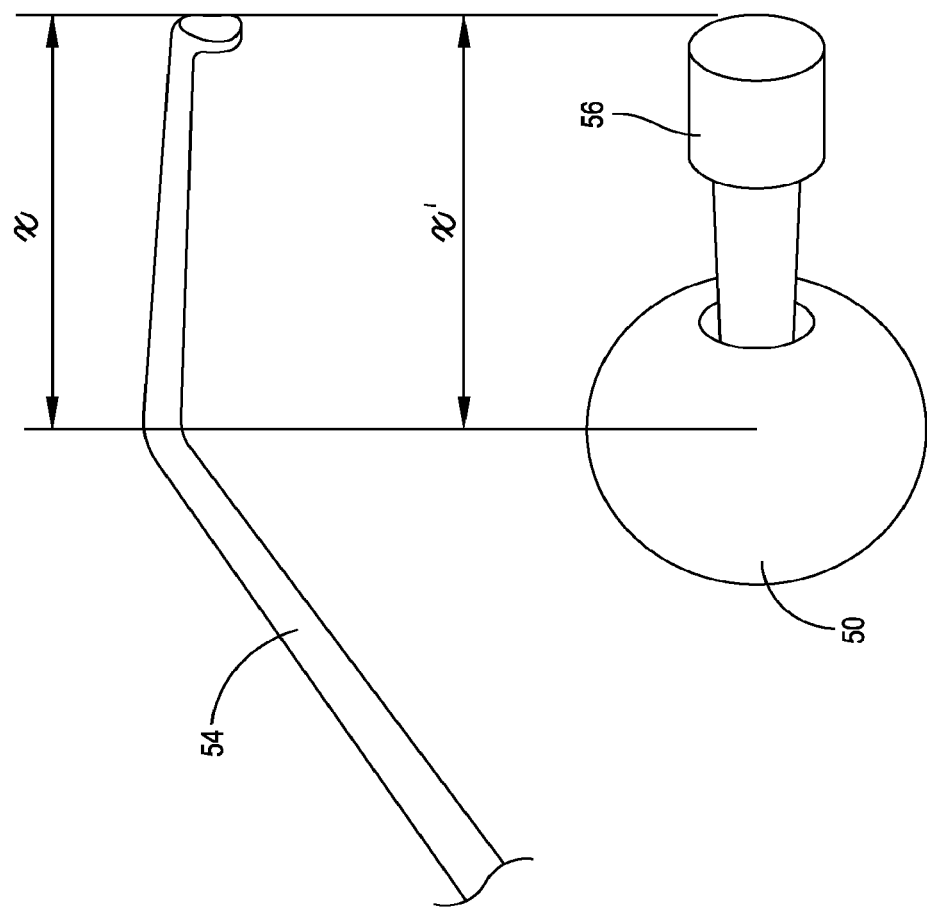

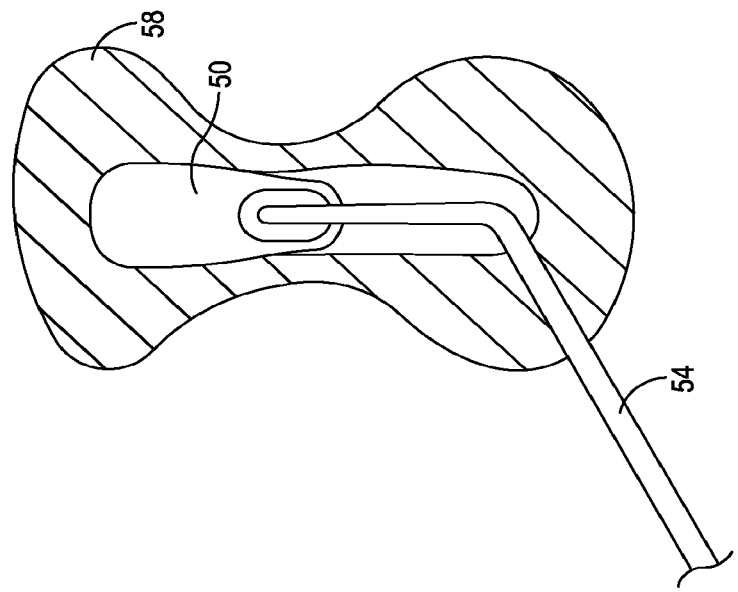
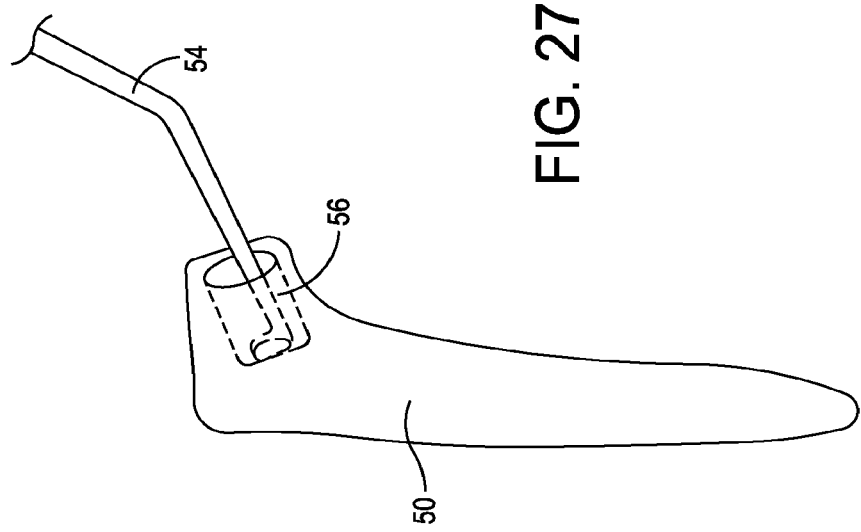

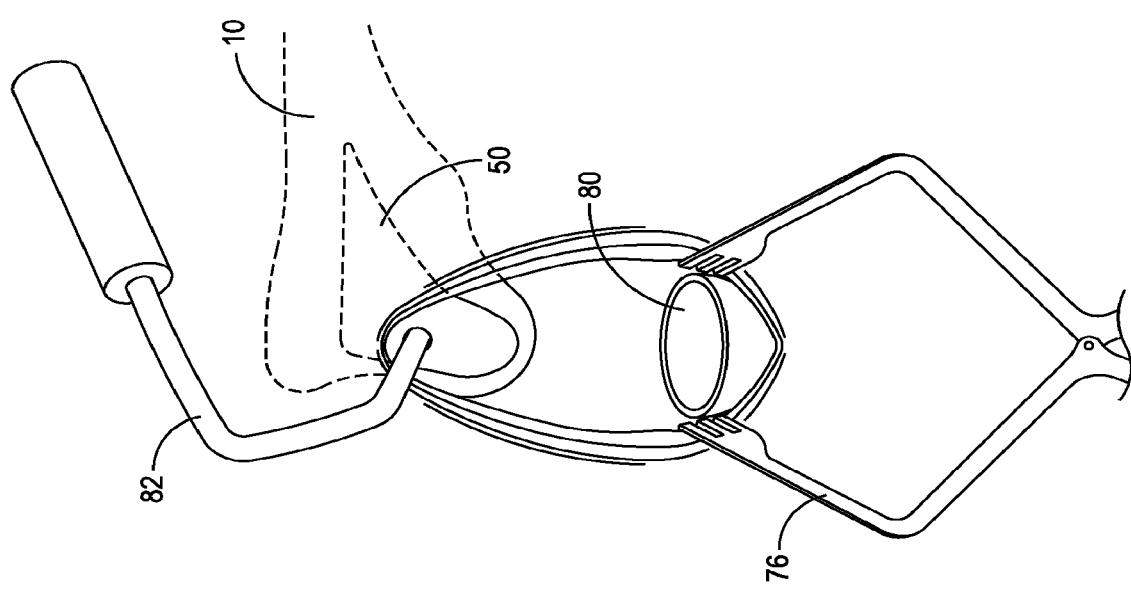

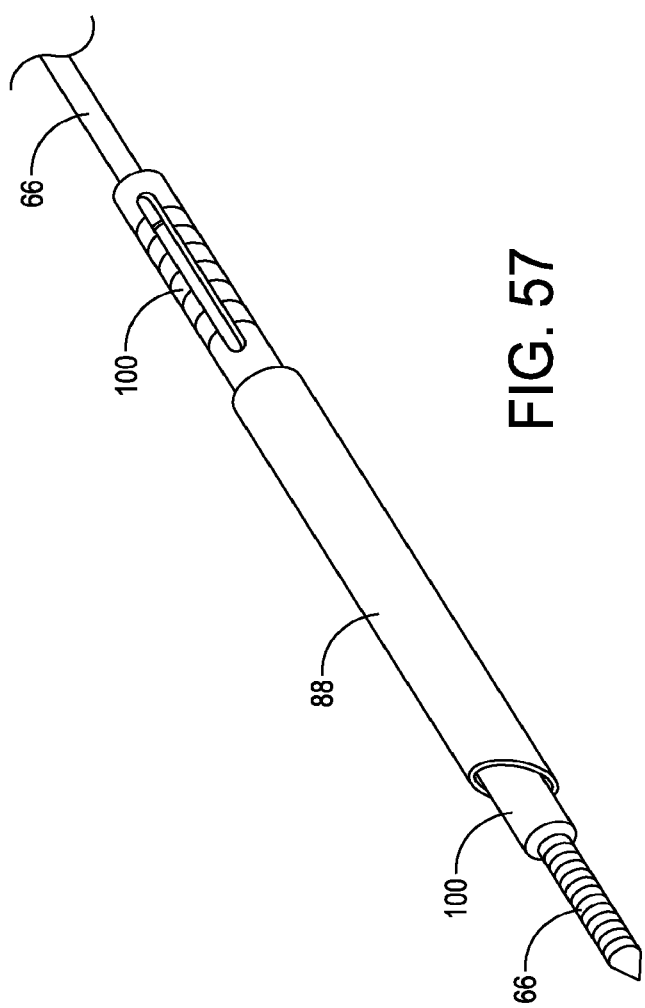
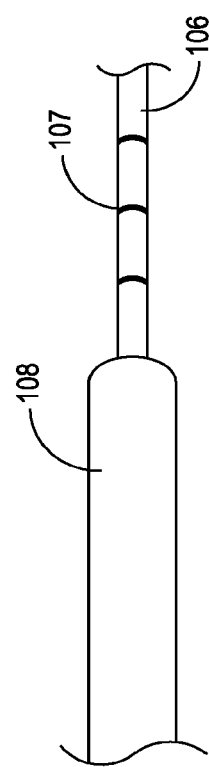
FIG. 57
FIG. 58

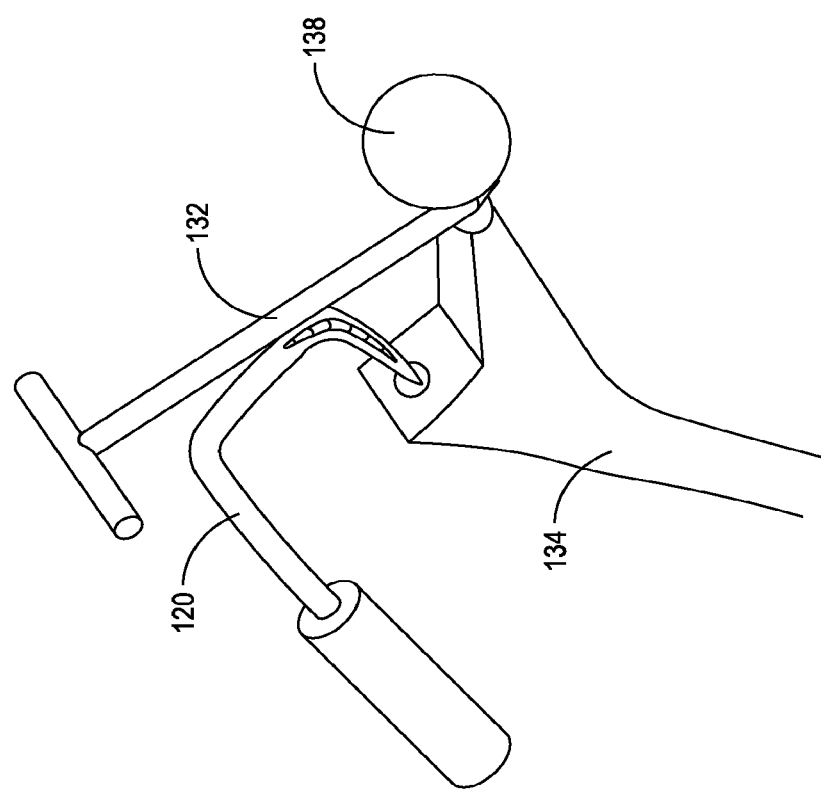

METHODS AND TOOLS FOR HIP REPLACEMENT WITH SUPERSCAPSULAR PERCUTANEOUSLY ASSISTED TOTAL HIP APPROACH

CROSS-REFERENCE TO RELATED APPLICATIONS

The present application claims priority to the following applications, which are incorporated by reference herein in their entireties: the present application is a continuation of U.S. patent application Ser. No. 16/686,512 filed Nov. 18, 2019, which is pending; U.S. patent application Ser. No. 16/686,512 claims priority to U.S. patent application Ser. No. 14/910,632, filed Feb. 5, 2016, which issued as U.S. Pat. No. 10,478,317 on Nov. 19, 2019; U.S. patent application Ser. No. 14/910,632 claims the benefit of PCT/IB2014/002418 filed August 6, which is expired; PCT/IB2014/002418 claims the benefit of U.S. Provisional Patent Application 61/862,865, filed Aug. 6, 2013.

FIELD OF DISCLOSURE

The disclosed devices, systems, methods and tools relate to surgical techniques. More particularly, the disclosed devices, systems, methods and tools relate to providing a replacement for a patient's hip with a minimal loss of blood, minimal tissue trauma, and a minimal length of operating time and patient recovery time.

BACKGROUND

Great progress has been made in the field of total hip arthroplasty (THA), commonly known as hip replacement. Hip replacements, particularly among the elderly, are now common. In spite of the considerable progress which has been made, many hip replacement operations still use relatively crude procedures. For example, it is common to make an incision of a relatively great length in a patient's hip as one of the first steps in a hip replacement operation. The incision may be as long as approximately eight inches (8") to approximately twelve inches (12"). Large incisions may increase operating time and cause patients to lose large amounts of blood, suffer significant trauma to surrounding tissues, and require longer recovery periods.

Examples of minimally invasive hip procedures are disclosed in U.S. Pat. No. 6,997,928, issued to Penenberg and titled "Apparatus for and Method of Providing a Hip Replacement," U.S. Pat. No. 7,105,028, issued to Murphy and titled "Tissue Preserving and Minimally Invasive Hip Replacement Surgical Procedure," U.S. Pat. No. 7,651,501, issued to Penenberg et al. and titled "Instrument for Use in Minimally Invasive Hip Surgery," and U.S. Pat. No. 7,833,229, issued to Penenberg and titled "Apparatus for and Method of Providing a Hip Replacement," each of which is incorporated by reference herein in its entirety. These patents also disclose numerous tools for use in performing the minimally invasive hip procedures. The devices, systems, and methods disclosed herein improve on the tools and methods disclosed in these patents.

SUMMARY OF THE INVENTION

The present disclosure provides a minimally invasive and tissue preserving surgical procedure for replacing a patient's hip joint with an artificial hip prosthesis, with a minimal loss of blood, minimal tissue trauma, and a minimal length of operating time and patient recovery time. The present disclosure also provides the related tools, devices, systems, and methods. These include but are not limited to the following examples.

In one aspect, an exemplary surgical procedure for replacing a hip joint is provided. In the surgical procedure, a patient is first placed in a lateral decubitus position on a peg board having at least two pegs. In some embodiments, at least two anterior pegs are placed against a pubic symphysis of the patient, to act as a femoral fulcrum to lever a proximal femur. A main incision is made on an operative leg. The main incision is initiated at a point being a projection of a tip of a greater trochanter and extends proximally about a distance in the range of from 1 cm to 8 cm (for example, in the range from 6 cm to 8 cm) in line with the femoral axis of the operative leg. An inline capsulotomy is made to expose the hip joint capsule for accessing the hip joint. The inline capsulotomy is performed while keeping muscles and posterior capsule intact. The surgical procedure further comprises preparing the femoral canal of the femur in the operative leg for receipt of a femoral implant, resecting and removing the femoral head of the femur, and performing a step of acetabular preparation using a retractor comprising two tip rails, each tip rail having a plurality of tines.

In some embodiments, the step of preparing the femoral canal comprises reaming the femur to enter the femoral canal and expand proximal opening therein, and broaching the femur by placing a femoral broach in the femoral canal for use as a template. The step of preparing the femoral canal may further comprise cutting and removing bone fragments using a round box cutter osteotome configured to cut a bone and remove bone fragments simultaneously while spinning in one direction.

In some embodiments, the step of resecting and removing the femoral head comprises inserting a first Schanz pin into a solid part of the femoral head, and moving the first Schanz pin to rotate the femoral head. The step of resecting and removing the femoral head may further comprise inserting a second Schanz pin into a different solid part of the femoral head, and moving the second Schanz pin to rotate the femoral head. The first Schanz pin or the second Schanz pin may comprise a tip having cross threads. In some embodiments, the first Schanz pin and the second Schanz pin point to different directions. The femoral head is rotated to tear the ligamentum teres or expose the ligamentum teres outside the acetabulum.

In some embodiments, a mobile window for showing the acetabulum of the femur is formed by sliding the retractor having the two tip rails along soft tissues. In some embodiments, the step of performing a step of acetabular preparation using a retractor having two tip rails with tines comprises placing a bone hook into a broach inside and along the femur. The bone hook and the two tip rails are configured to form a three-point capsular distraction. The surgical procedure may further comprise holding an acetabular cup and moving the acetabulum cup into the acetabulum of the femur.

In some embodiments, the surgical procedure further comprises a step of dissection or retraction of tissues of different tissue planes. The step of dissection or retraction comprises the steps of placing a sharp dissector between a first two tissue planes, and placing a retractor along inner space of the sharp dissector between the first two tissue planes. The step of dissection or retraction further comprises removing the sharp dissector, placing the sharp dissector between a second two tissue planes, removing the retractor between the first two tissue planes, and placing the retractor along inner space of the sharp dissector.

In some embodiments, the surgical procedure further comprises the following steps: reaming the acetabulum by placing and rotating a reamer basket in the main incision using a reamer basket holder, placing and aligning an acetabular cup into the acetabulum, trying a trial neck and a trial head, disassembling the trial neck and the trial head, and assembling implants for the hip joint. A screw can be also placed into the acetabular cup through a pilot hole, which is drilled to a predetermined depth with the aid of a depth gauge.

In some embodiments, in the step of disassembling the trial neck and the trial head, the tip end of a bone hook tool is placed into a hole of a trial part. The trial part is connected to the trial neck. The bone hook tool comprises a bent tip with an indented surface as described herein. A tip of a blunt trocar having a round surface is placed into a hole on the trial neck. The round surface of the blunt trocar is engaged with the indented surface of the bent tip of the bone hook tool. The blunt trocar is rotated against the indented surface of the bone hook tool to move the tip of the blunt trocar away from the tip end of the bone hook tool.

In another aspect, the present disclosure provides different tools suitable for the surgical procedure. For example, in some embodiments, the present disclosure provides a retractor for acetabular preparation in a surgical procedure of replacing a hip joint. Such a retractor comprises two tip rails. Each tip rail comprises a plurality of tines substantially parallel to each other and to the respective tip rail. In one embodiment, the plurality of tines are symmetrically distributed on both sides along each tip rail. In another embodiment, each tip rail is straight to the end and has only the plurality of tines on one side of the respective tip rail. The retractor further comprises two arms. Each respective arm is at an angle to each respective tip rail. The retractor is configured to be able to slide along soft tissues to show an acetabulum in surgical procedure of replacing a hip joint, and an acetabular cup can be held and moved to the acetabulum. A method of using such a retractor is also provided in this disclosure.

In some embodiments, the present disclosure provides a bone hook tool. The bone hook tool comprises a bent tip with an indented surface on an outer side of the bent tip. The indented surface is configured to accept a convex surface of a second tool (e.g., a blunt trocar) to remove or disassemble a part to be removed (e.g., a trial neck) from a trial part or an implant without any dislocation. The indented surface is configured to accept a round surface of the second tool. The indented surface may be smooth or textured. The bone hook is configured to be engaged with the second tool with a tip end of the bent tip inserted into a hole on the trial part or the implant and a tip of the second tool inserted into a hole on the part to be removed. The second tool is rotated against the indented surface of the bone hook tool. The part to be removed is disassembled when the tip of the second tool are moved away from the tip end of the bone hook tool. A method of using such a bone hook tool is also provided in this disclosure.

In some embodiments, the present disclosure provides a depth gauge for centering a screw in a surgical procedure. The depth gauge comprises a body, and a first end and a second end. The body may be straight and cylindrical. The first end comprises a screw head or is adapted to be coupled with a screw head. The second end comprises depth marks. In some embodiments, the depth gauge has an outer diameter and is configured to pass through a cannula having an inner diameter larger than the outer diameter of the depth gauge. The depth gauge has an inner diameter and is so configured that a pin (e.g., a Schanz pin) can pass through the depth gauge. The depth marks in the second end of the depth gauge are configured to indicate and control the depth of insertion of the pin. A method of using such a depth gauge is also provided in this disclosure.

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

FIGS. 7-12 illustrate an exemplary method of retraction using the placement and replacement techniques in some embodiments.

FIG. 25 illustrates a step of resecting femoral head in some embodiments.

FIGS. 26-28 illustrate exemplary tools and an exemplary method of measuring the femoral head before resecting the femoral head in accordance with some embodiments.

FIGS. 40-42 illustrate exemplary methods of using the modified Zelpi retractor of FIGS. 37-39 in some embodiments.

FIGS. 56-57 illustrate a method of using the depth gauge of FIG. 57 in some embodiments.

FIG. 58 illustrates an alternative tool or method of having depth marks on a pin or drill in some embodiments.

FIGS. 64-68 illustrate exemplary method of using the bone hook tool of FIGS. 61-63 in some embodiments.

DETAILED DESCRIPTION

Figure 1:
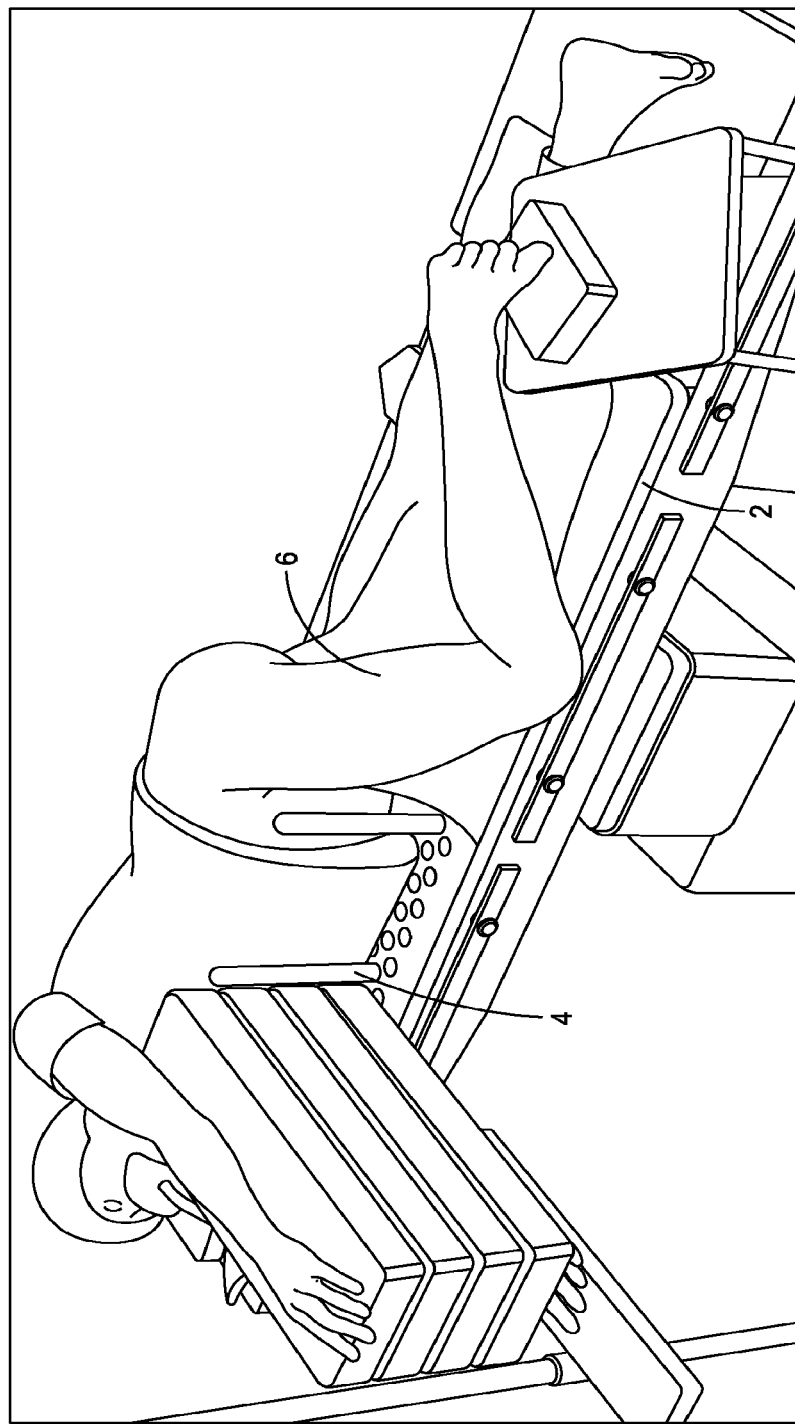
FIG. 1 illustrates a "home position" of a patient lying on a peg board in accordance with some embodiments.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

The posterior approach is considered the gold standard of total hip arthroplasty (THA), commonly known as a hip replacement, allowing access to the hip joint for the placement of components without any femoral head size limitation. Specifically, the posterior approach allows for the use of big femoral head prostheses and ream-and-broach or broach-only femoral stems.

This invention provides devices, systems, methods and tools for hip replacements with supercapsular percutaneously assisted total hip (SUPERPATH™) approach, which is a modification of the standard posterior approach, with the added benefit of allowing for the short external rotators to remain intact. Preservation of these muscles can decrease operative time, post-operative recovery and intra-operative blood loss, and increase post-operative stability while requiring fewer post-operative movement restrictions. This approach maintains all of the advantages of the standard posterior approach and is also extensile, being easily converted to the standard posterior approach, making it easy to learn and providing the surgeon complete freedom during the operation. The resulting surgical technique provides a replacement for a patient's hip with a minimal loss of blood, minimal tissue trauma, a minimal length of operating time and patient recovery time.

The necessary size of a THA incision decreases as the angular constraints of the femoral component and acetabular reamers are addressed. Modularity in the design of the femoral component allows access to the femur in a manner similar to an intermedullary (IM) rod—that being directly superior. With the SUPERPATH™ approach, acetabular preparation can be performed through a percutaneous incision.

Accessing the femur through the trochanteric fossa with the femoral head intact absorbs some hoop stresses during reaming and allows for less chance of fracture associated with the insertion of noncemented femoral components. To prevent varus orientation of these components, a lateralizing trochanteric reamer is recommended.

Additionally, offset is easily determined after broaching the femur with the head in situ. When the appropriate size broach is seated, the neck osteotomy permits precise resection of the neck—representing the exact offset without major acetabular deformity.

Acetabular preparation is performed through a small portal incision, allowing medialization with the reamers. Direct visualization allows precise placement of the acetabular component. Working through a cannula, the leg can be moved to easily access all boundaries of the acetabulum, regardless of patient anatomy. In addition, acetabular preparation will not be obstructed by the greater trochanter or the proximal femur. And using an alignment handle and a blunt trocar, the risk of damaging the sciatic nerve is minimized, with a safe zone posterior to the femur of at least 2.5 cm.

The tools, devices, instruments, systems, implants, methods and surgical procedures provided in this disclosure are for use in total hip arthroplasty for reduction or relief of pain and/or improved hip function in skeletally mature patients. The indications for use include but are not limited to non-inflammatory degenerative joint disease such as osteoarthritis, avascular necrosis, ankylosis, protrusio acetabuli, and painful hip dysplasia; inflammatory degenerative joint disease such as rheumatoid arthritis; correction of functional deformity; and revision procedures where other treatments or devices have failed.

The devices, systems, methods and tools provided in this disclosure are described based on a general sequence of the surgery. In the drawings, like items are indicated by like reference numerals, and for brevity, descriptions of the structure, provided above with reference to the previous figures, are not repeated. The methods or surgical techniques are described with reference to the exemplary structure described in the corresponding drawings. A surgical technique guide, titled "SUPERPATH™ Micro-Posterior Approach, SURGICAL TECHNIQUE," published by Wright Medical Technology, Inc. (a part of which becomes Microport Scientific Corporation) in 2012 (No. MH382-512, hereinafter "Surgical Technique Guide"), is incorporated by references herein in its entirety. Some tools are described with reference to respective part or product numbers (P/N) described in the SURGICAL TECHNIQUE or other product brochures. All the tools and devices described in the present disclosure can be made of a suitable material, including but not limited to metal, plastics or any combinations thereof.

Accurate preoperative templating requires good quality standardized radiographs of the pelvis and operative hip. Preoperative templating may be used for estimation purposes. Final component size and position can be accurately determined intraoperatively. For example, X-ray templates may be used to estimate the size of the product to be used. The anatomy of the patient ultimately determines the size of the product for an individual patient.

(1) Patient Positioning

As shown in FIG. 1, a patient is placed in a lateral decubitus position in a location comfortable for the operating surgeon. A peg board 2 with pegs 4 is used for patient positioning. Pegs 4 may be radiolucent. The operative leg 6 for the surgery faces up as shown in FIG. 1. In some embodiments, due to the nature of this technique, it may not be needed to bias the location of the patient to the anterior edge of the operating table as maximal leg adduction is not needed.

In some embodiments, a peg board 2 comprises at least two pegs 4 configured to match the locations of the patient's body: two long pegs at the pubic symphysis, two long pegs at the sacrum, a long peg at the chest level and just below the breast, a long peg at the shoulder blades.

To ensure appropriate pelvic rotation, bias the hip to lean slightly posterior. Flex the operative hip 45° and internally rotate the operative leg 10°-15° to present the greater trochanter upward. With the operative foot resting on a padded mayo stand and the leg in slight adduction, the weight of the leg 6 will balance the hip, bringing the pelvis to neutral rotation. This is the "home position" of the technique as the operative leg 6 will remain there for most of the procedure.

Figure 2:
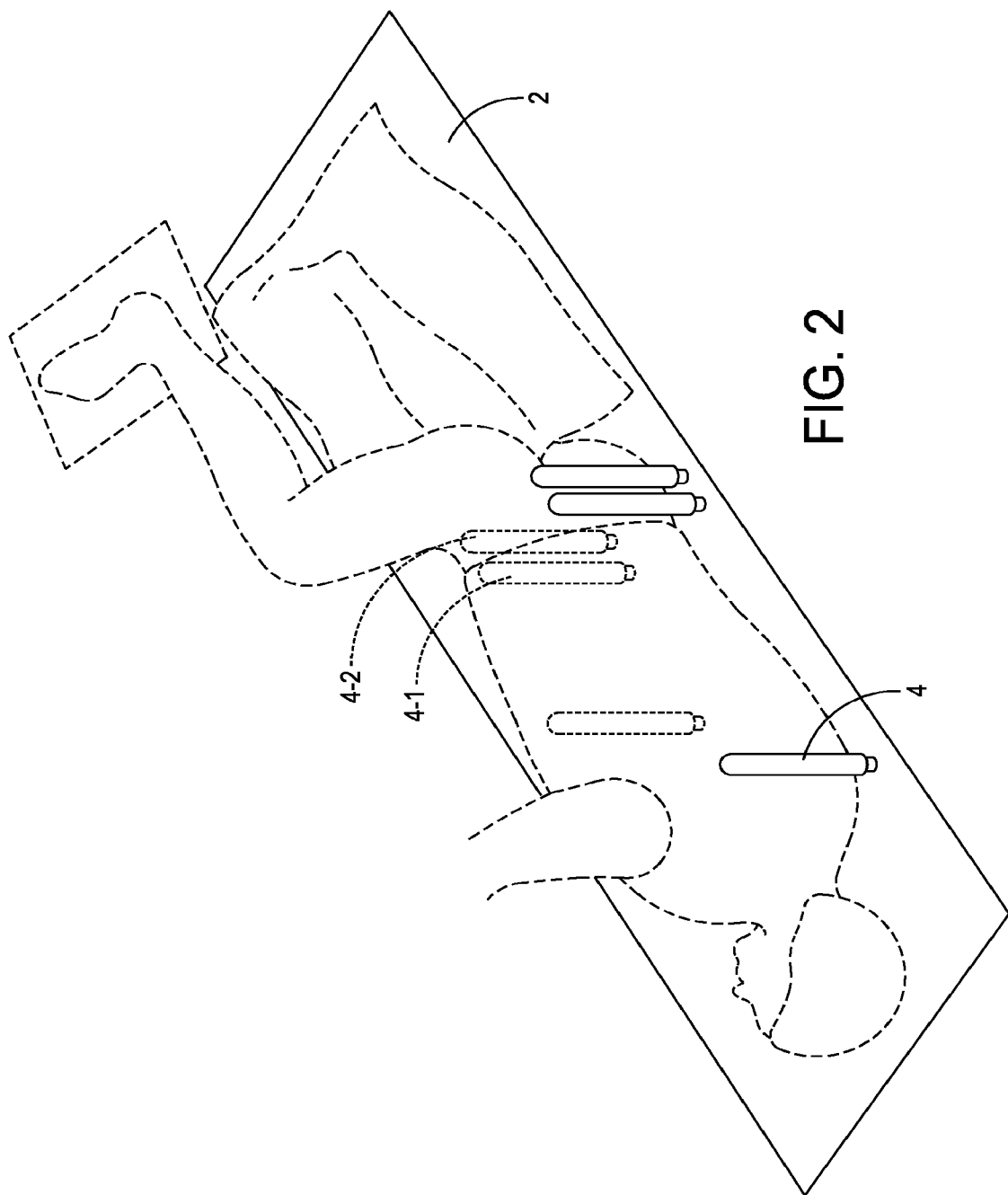
FIG. 2 illustrates an exemplary peg board in some embodiments.
Figure 3:
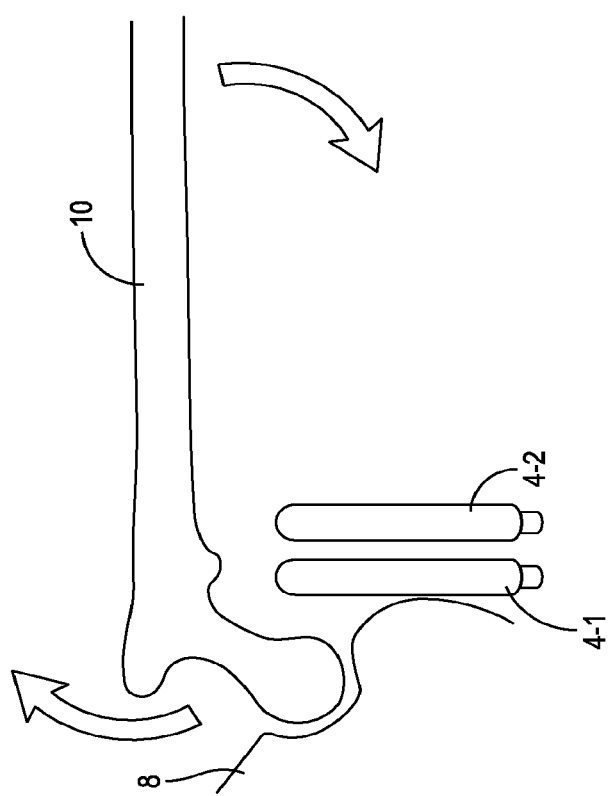
FIG. 3 is an enlarged fragmentary sectional view illustrating patient positioning on the peg board of FIG. 2 in some embodiments.

Referring to FIG. 2, an exemplary peg board 2 is used for positioning a patient in some embodiments. Pegs 4-1 and 4-2 as anterior pegs are placed against pubic symphysis of the patient, and act as a femoral fulcrum to lever the proximal femur 10 out of the socket. Pegs 4-1 and 4-2 also prevents anterior "rolling" of pelvis 8. Referring to FIG. 3, an enlarged view illustrates the patient positioning on the peg board 2 of FIG. 2. In this method of positioning the patient, a downward pressure exists on the knee and the operative leg 6. The hip is "lifted" out the socket without any twisting. This positioning method does not require additional soft-tissue dissection due to mechanical advantage.

(2) Soft Tissue Dissection

Figure 4:
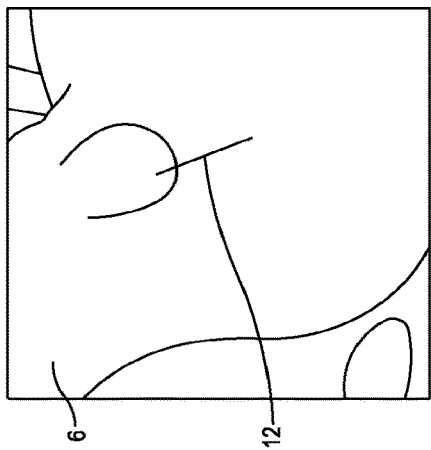
FIGS. 4-6 illustrate a method of making an incision of soft tissues on an operative leg in some embodiments.
Figure 6:
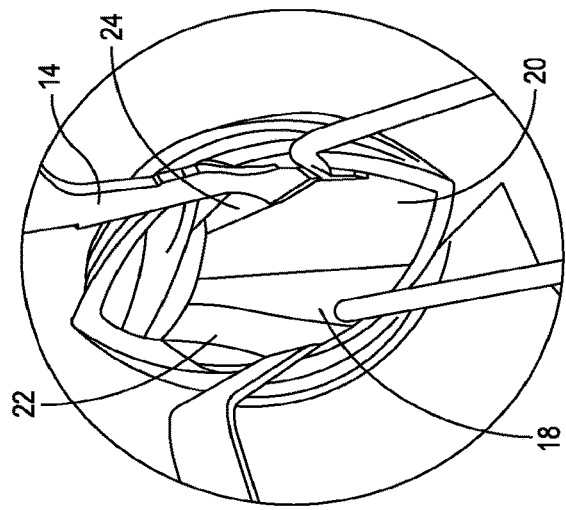
Figure 5:
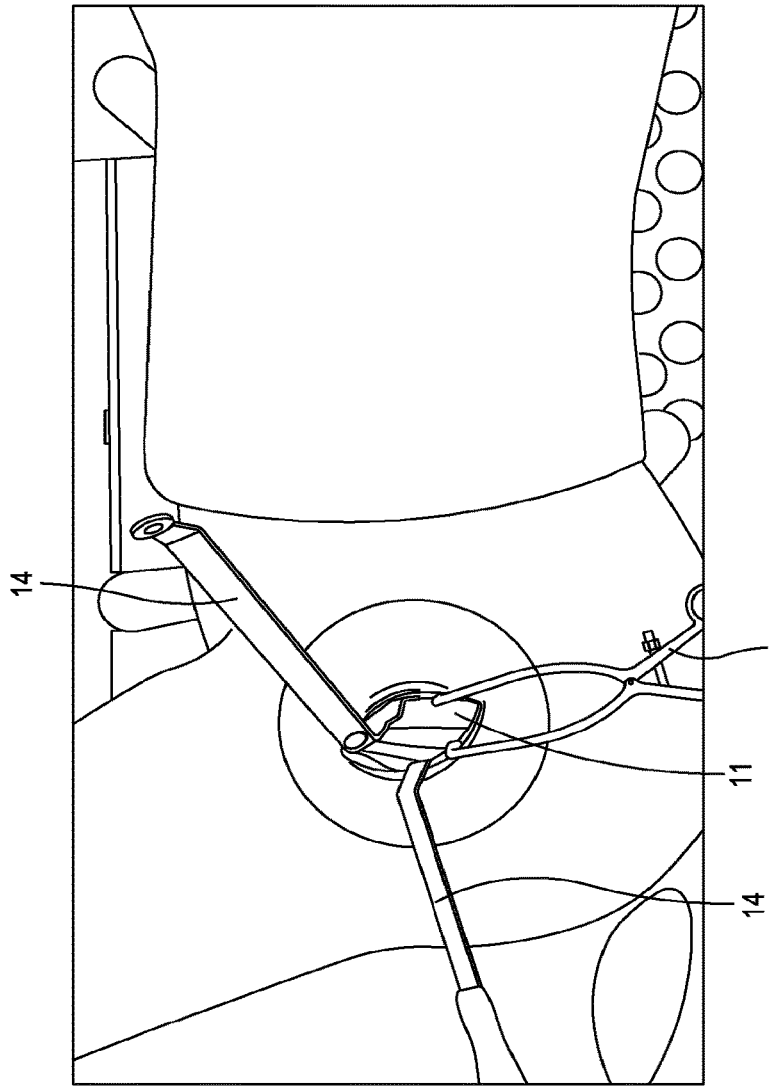

Referring to FIGS. 4-6, in an exemplary method of making a main incision 12 of soft tissues on an operative leg 6 for subsequent accessing a hip joint in some embodiments, the main incision 12 is initiated at a point which is a projection of a tip of a greater trochanter and extends proximally about a suitable distance of 8 cm or less, for example, in the range from 1 cm to 8 cm. In some embodiments, the incision 12 is extended about 6-8 cm proximal, in line with the femoral axis (as shown in FIG. 4). The incision 12 is made to the level of the gluteus maximus investing fascia 11. The fascia 11 is then incised using electrocautery, starting at the tip of the greater trochanter and extending in line with the main incision 12.

The operative leg 6 can be flexed, extended or adducted to adjust visualization through the main incision 12. In some embodiments, two wing-tipped elevators (e.g., P/N 20070038; angled versions may also be used, e.g., P/N 20070040) are used to split the gluteus maximus, exposing the bursa overlaying the gluteus medius. A very thin layer of bursa tissue is carefully incised along the posterior border of the gluteus medius.

A Cobb elevator is placed under the gluteus medius, then replaced with a blunt Hohmann retractor 14 (e.g., P/N 20073114). An assistant can use gentle pressure to maintain position of the retractors 14 and 16 while protecting the gluteus medius. In some embodiments, the blade of the blunt Hohmann retractor 14 are not be forced beyond 90° from the wound and now is resting in the interval between the gluteus medius and gluteus minimus. Sometimes the release of short, external rotators may be necessary, especially in tight hips.

After dissecting soft tissue, the incision 12 is shown in FIGS. 5 and 6. FIG. 6 is an enlarged view of the incision 12 and resulting hip socket. Different muscles without any damages can be seen. For example, these muscles may include superior gemellus muscle 18, piriformis muscle 20, obturator intermus muscle 22, and gluteus minimus muscle 24.

Referring to FIGS. 7-12, an exemplary method for dissection or retraction (or both) is used in the step of soft tissue dissection (or the subsequent step of capsular exposure and any other suitable step in the surgical procedures) in some embodiments. This method can be also used for dissection or retraction (or both) of any tissue involving different tissue planes, either horizontally or vertically. This exemplary method, using techniques of placement and replacement, comprises the steps described as follows with references to FIGS. 7-12.

Referring to FIG. 7, a sharp dissector (or retractor) such as a Cobb elevator 28 is placed toward and inserted into a tissue 26 having three tissue planes 26-1, 26-2 and 26-3. Three tissue planes 26-1, 26-2 and 26-3 can be oriented in any direction, including but not limited to either horizontally or vertically. FIG. 7 and any other drawings in FIGS. 8-12 can be interpreted as a top down view, a sectional view or a view from any other direction. Even though parallel tissue planes are shown in FIGS. 7-12, the tissue planes are not necessarily parallel in some other embodiments.

FIG. 8 illustrates that a sharp dissector such as a Cobb elevator 28 is placed in between a first two tissue planes, for example, between tissue planes 26-1 and 26-2. The step of placing the Cobb elevator 28 can be performed while dissecting soft tissues.

Figure 9:
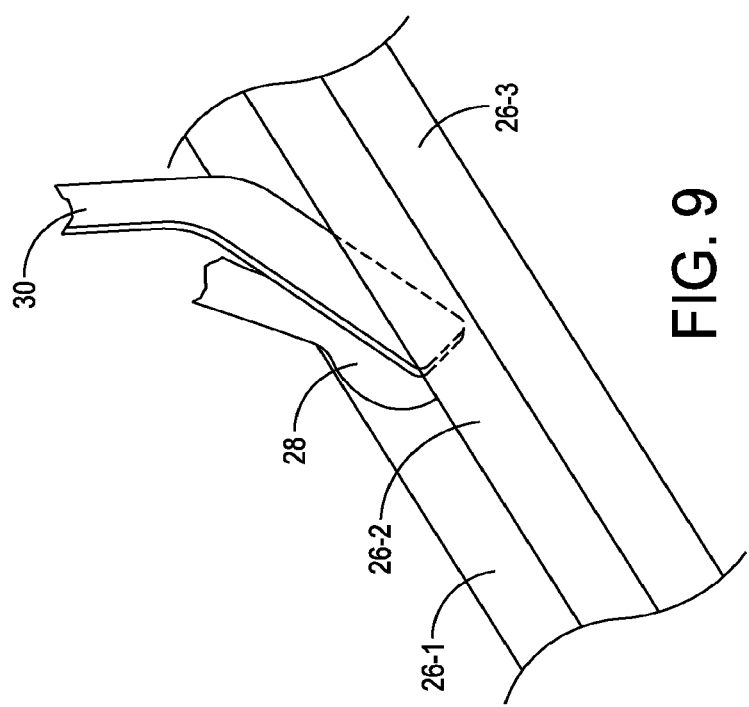

Referring to FIG. 9, a retractor such as a blunt Hohmann retractor 30 is placed along inner space of the Cobb elevator 28 after the Cobb elevator 28 is placed in between two tissue planes (26-1 and 26-2).

Figure 10:
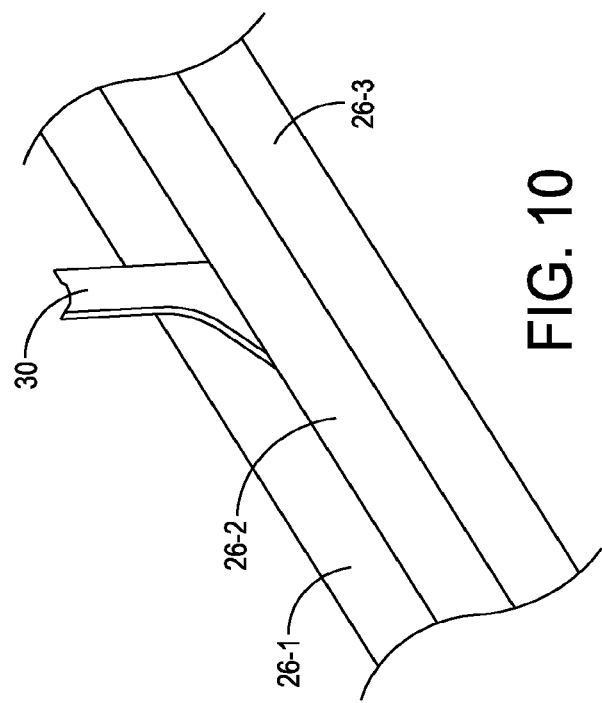

Referring to FIG. 10, the sharp dissector such as the Cobb elevator 28 is removed. The retractor 30 is positioned between tissue planes 26-1 and 26-2 for retracting, and also provides temporary visibility for further dissection.

Referring to FIG. 11, the sharp dissector such as the Cobb elevator 28 is placed into (or used to dissect) a new interval or between two different tissue planes such as a second two tissue planes 26-2 and 26-3.

Referring to FIG. 12, the retractor such as the blunt Hohmann retractor 30 is removed from the space between tissue planes 26-1 and 26-2, and placed along inner space of the Cobb elevator 28 at the new interval, for example, between tissue planes 26-2 and 26-3.

The Cobb elevator 28 is then removed, and these steps are repeated if needed.

This exemplary method of FIGS. 7-12 with reduced invasiveness is referred as a "swimming" method of dissection and retraction. This method offers several advantages. For example, dissection is made only for what is required for retractor placement. Specialized dissectors and retractors that are matched in size are used. Additional dissection is avoided. This method may be used in existing potential spaces between structures, or in newly created spaces.

(3) Capsular Exposure

Figure 14:
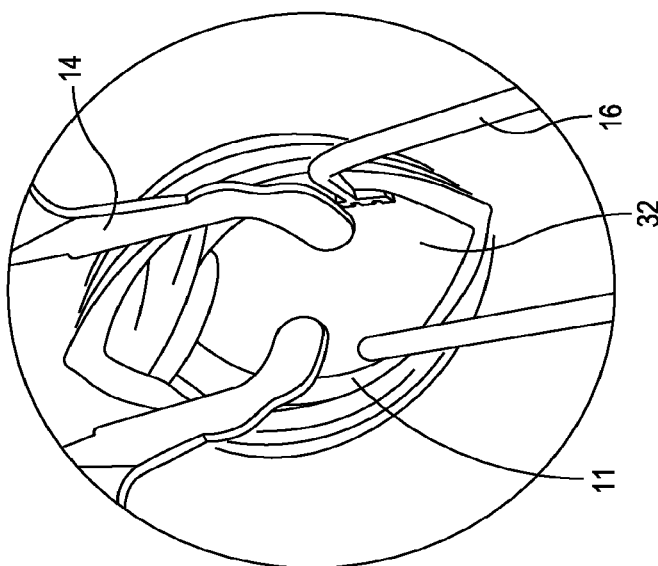
FIGS. 13-14 illustrate a step of capsular exposure in some embodiments.
Figure 13:
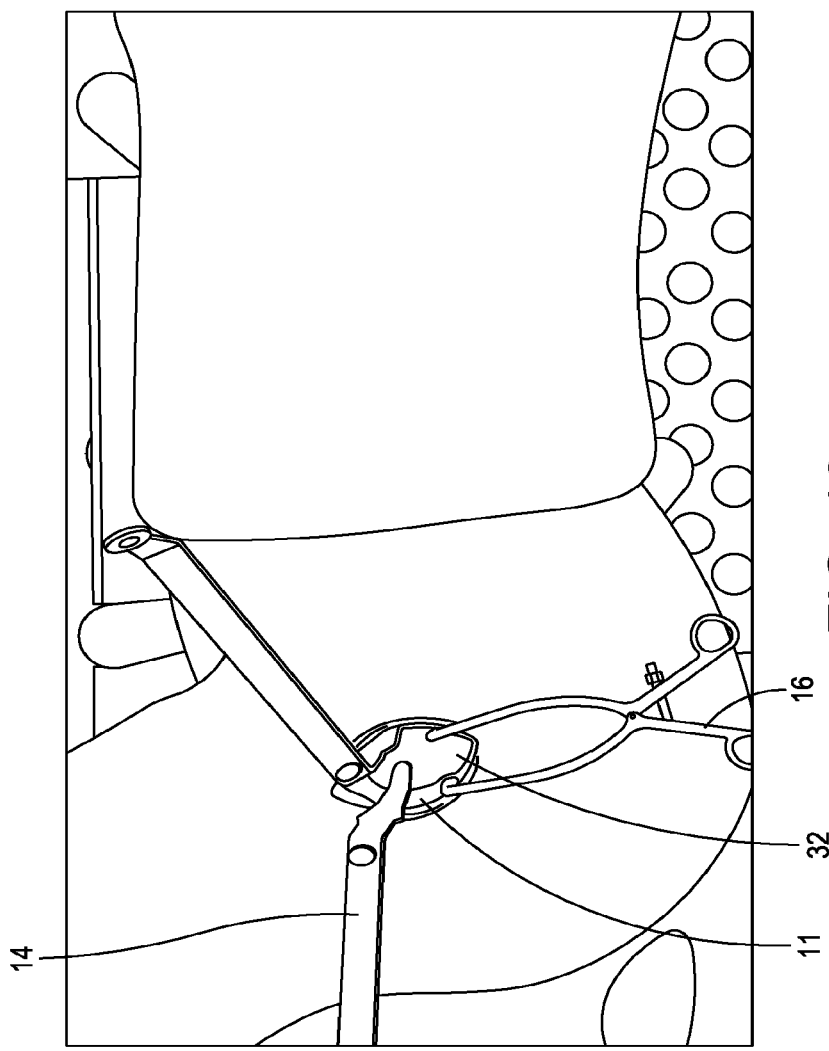

With an assistant abducting and externally rotating the hip (raise the knee while keeping the foot on the Mayo stand) to decrease tension in the external rotators, a surgeon can place a Cobb elevator 28 posteriorly between the piriformis tendon 20 and the gluteus minimus 24. The sciatic nerve will be protected by the external rotators. The Cobb elevator 28 is then replaced with a blunt Hohmann retractor 14, with the blunt Hohmann 14 now resting between the posterior capsule (hip joint capsule) 32 and the external rotators. The blade of the blunt Hohmann retractor 14 should not be forced beyond 90°, and the handles of the Hohmann retractors 14 should be parallel to one another. The knee is then lowered, and the leg returned to the "home position." If excessive force is generated by the piriformis tendon 20, it can be released at this time under direct visualization. After the step of capsular exposure, the exposed capsule 32 is illustrated in FIGS. 13-14.

Figure 15:
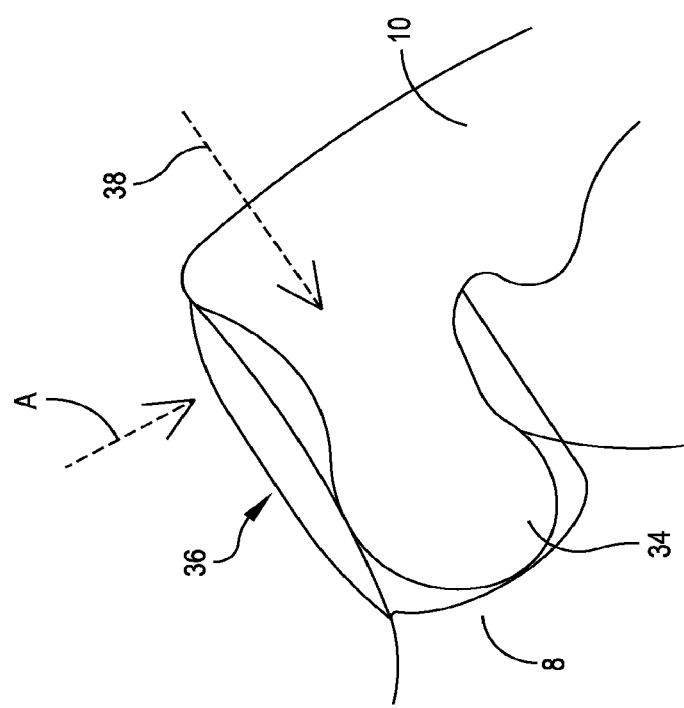
FIGS. 15-16 illustrate an exemplary method of inline capsulotomy in some embodiments.
Figure 16:
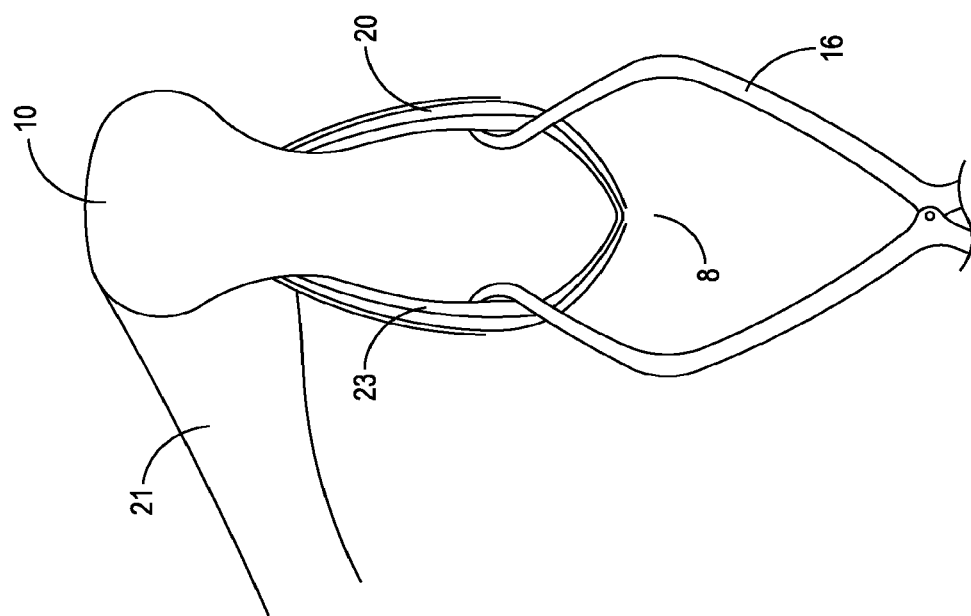

As intra-operative views, FIGS. 15-16 illustrate an exemplary method of inline capsulotomy 36 to expose the hip joint capsule 32 for accessing the hip joint in some embodiments. "A" and "P" in FIGS. 15-16 represent "anterior" and "posterior," respectively. FIG. 15 is a sectional view of the incision site in preparation for the capsulotomy 36. Femoral head 34, femoral neck, and the greater trochanter 38 are shown in or around the capsule 32 relative to the locations of pelvis 8 and femur 10. FIG. 16 is a top-down view illustrating the inline capsulotomy 36. Retractor 16 is shown relative to the locations of piriformis muscle 20, medius muscle 21 and minimus muscle 23.

Inline capsulotomy 36 allows for keeping piriformis muscle 20 and posterior capsule intact for in-situ total hip arthroplasty (THA). Inline capsulotomy 36 facilitates all soft-tissue retraction due to the effect of "reverse tent." The hip is placed in flexion, slight adduction and slight internal rotation. Inline capsulotomy 36 maintains tension from retractors 16. The access to the hip joint will allow for a superior (vertical) capsulotomy to be performed on the hip joint. Inline capsulotomy 36 facilitates anatomic closure, "rotator-cuff repair," and water-tight closure.

(4) Capsular Incision

Figure 18:
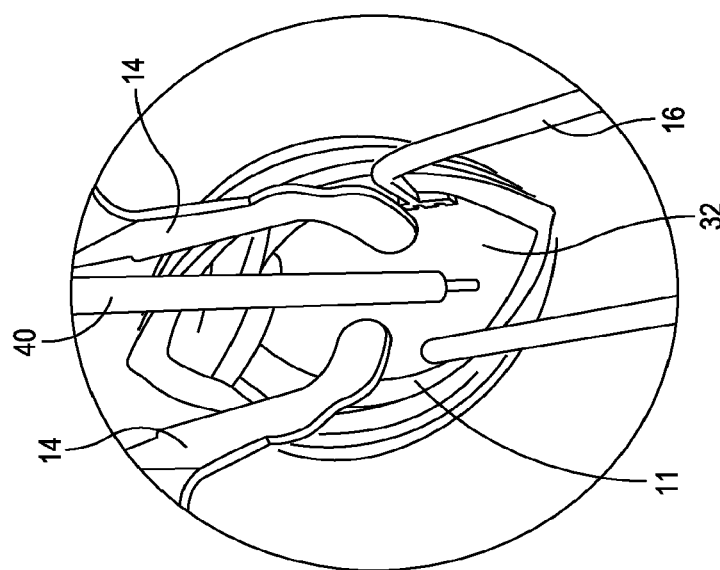
FIGS. 17-18 illustrate a step of capsular incision in some embodiments.
Figure 17:
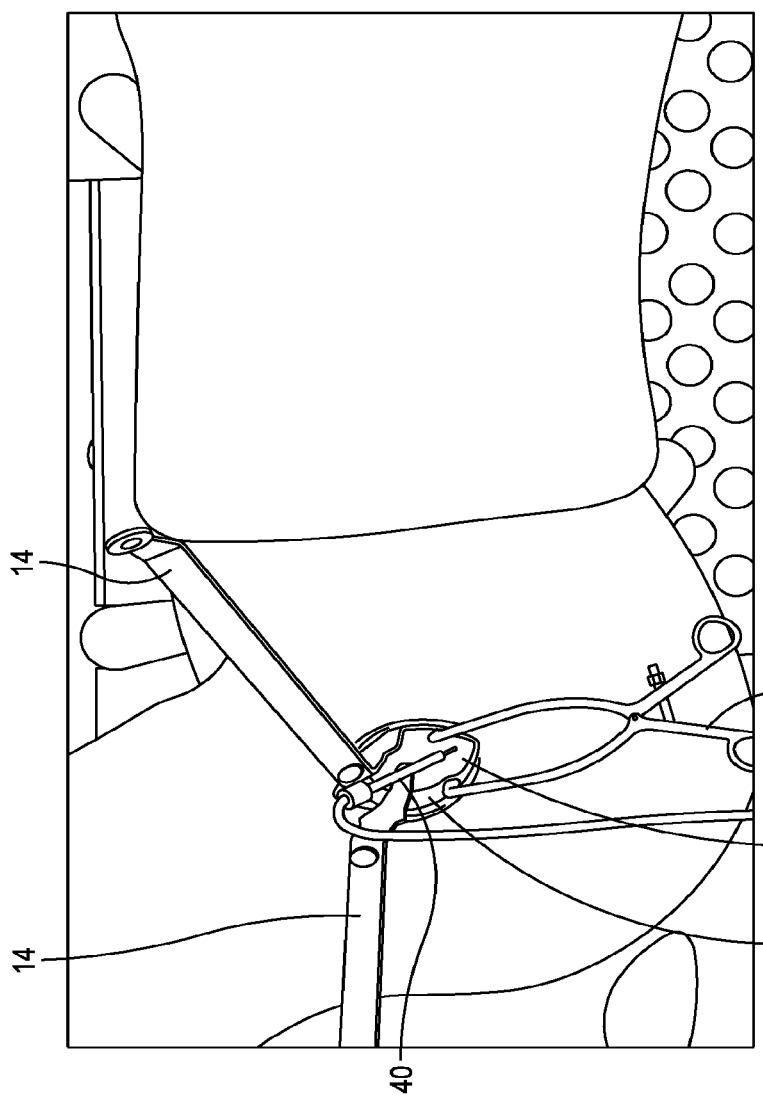

Referring to FIGS. 17-18, a step of capsular incision is performed. FIG. 18 is an enlarged view of the incision area of FIG. 17.

Use a Cobb elevator 28 to gently push the posterior border of the gluteus minimus 24 anteriorly to expose the underlying capsule 32. The capsule 32 is then incised in-line with the main incision 12 using electrocautery 40. In some embodiments, electrocautery 40 with a long tip is used to incise the trochanteric fossa to prevent bleeding of the anastomosis around the base of the femoral neck. Complete preparation of the entire saddle portion of the femoral neck and greater trochanter is ensured using electrocautery 40. Over-preparation is better than under-preparation in regards to reducing bleeding amongst the many recurrent vessels in this area. The capsulotomy is extended from the saddle of the femoral neck to 1cm proximally on the acetabulum.

The 1 cm capsular attachment subperiosteally can be carefully peeled off of the acetabular rim, extending 1cm anteriorly and posteriorly. This part of the dissection can be limited to only 1 cm in all directions. An assistant can notify the surgeon of any foot movement as the sciatic nerve lies 2 cm posteriorly. The capsular incision should be a simple, straight line and will be repaired like a rotator cuff in the end.

With an assistant lifting the knee to decrease external rotator tension, a Cobb elevator 28 is placed intra-articularly between the posterior capsule and the posterior femoral neck. The Cobb elevator 28 is then replaced with the blunt Hohmann retractor 14 that was previously located at the posterior capsule, and the leg is returned to the "home position." The anterior blunt Hohmann retractor 14 is re-positioned intra-articularly in a similar fashion. The capsule is tagged for identification during repair, and the piriformis fossa, the tip of greater trochanter and the anterior femoral neck (Saddle) are isolated.

(5) Femoral Preparation

Referring to FIGS. 19-22, a step of femoral preparation is performed in some embodiments. The femur 10 is reamed and broached with the head intact to minimize the risk of a femoral neck fracture. The step of femoral preparation includes reaming the femur to enter the femoral canal and expand proximal opening therein. With an assistant applying gentle adduction pressure to the knee of the patient, the saddle of the femoral neck is presented into the incision.

Figure 19:
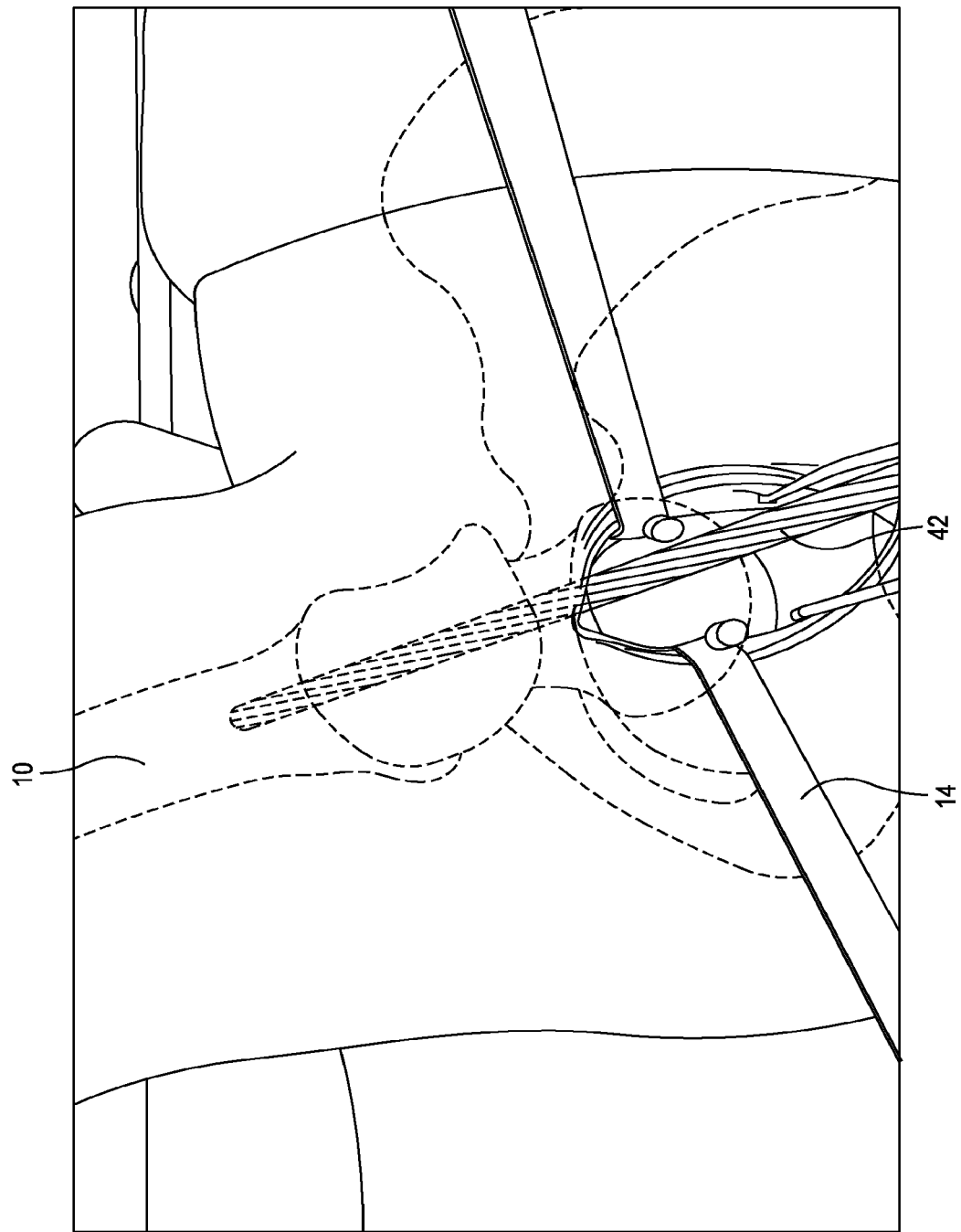
FIGS. 19-22 illustrate a method of femoral preparation in some embodiments.
Figure 20:
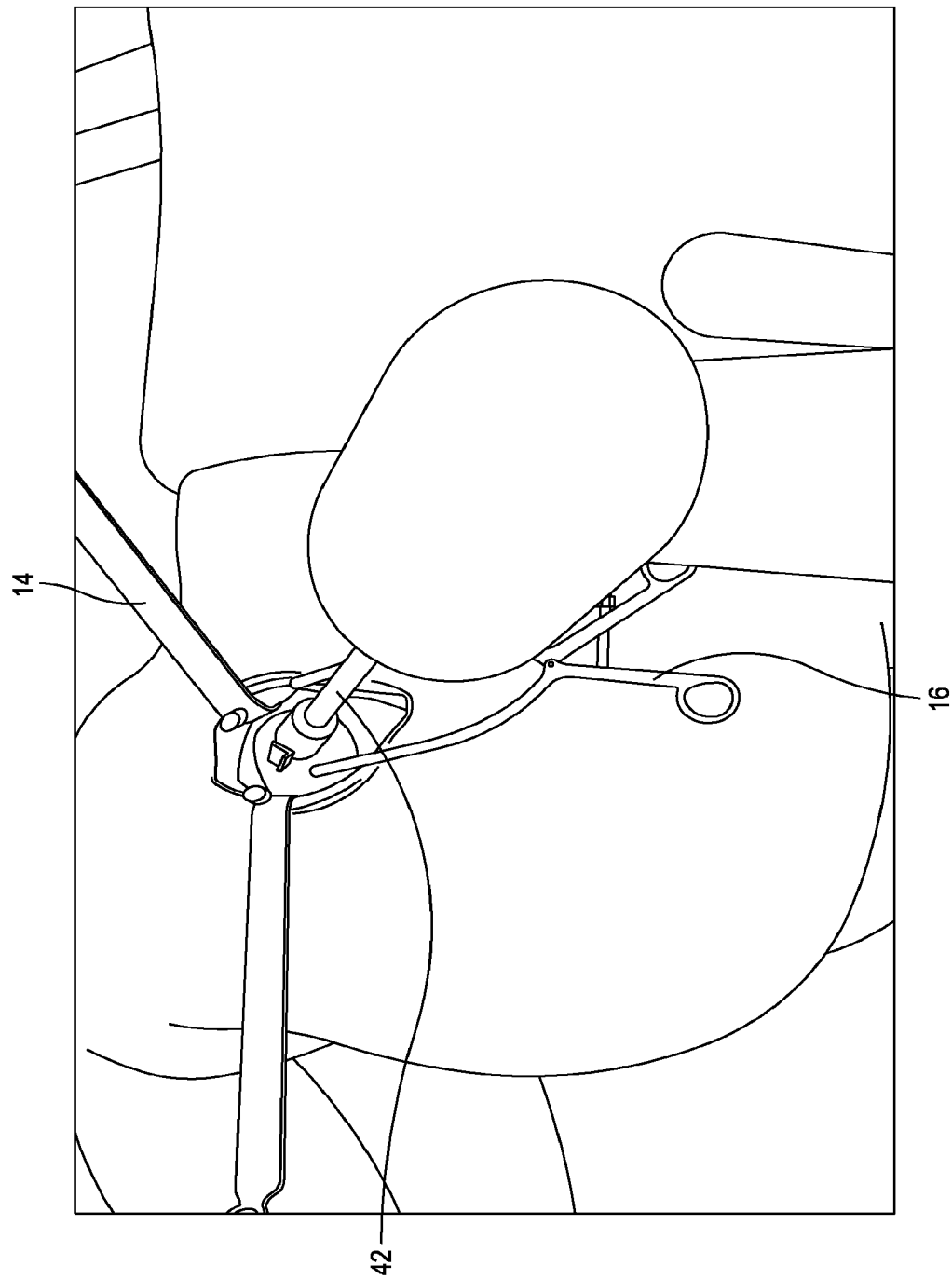

As shown from FIG. 19 to FIG. 20, a reamer 42 such as a starter reamer (for example, with a product number P/N PRR00080 or 4700R09000) is used to enter the femoral canal through the trochanteric fossa. Another reamer 42 such as a metaphyseal reamer (e.g., P/N PTMR0001) can be used to expand the proximal opening, ensuring that subsequent instruments are properly aligned and not positioned in varus.

Figure 21:
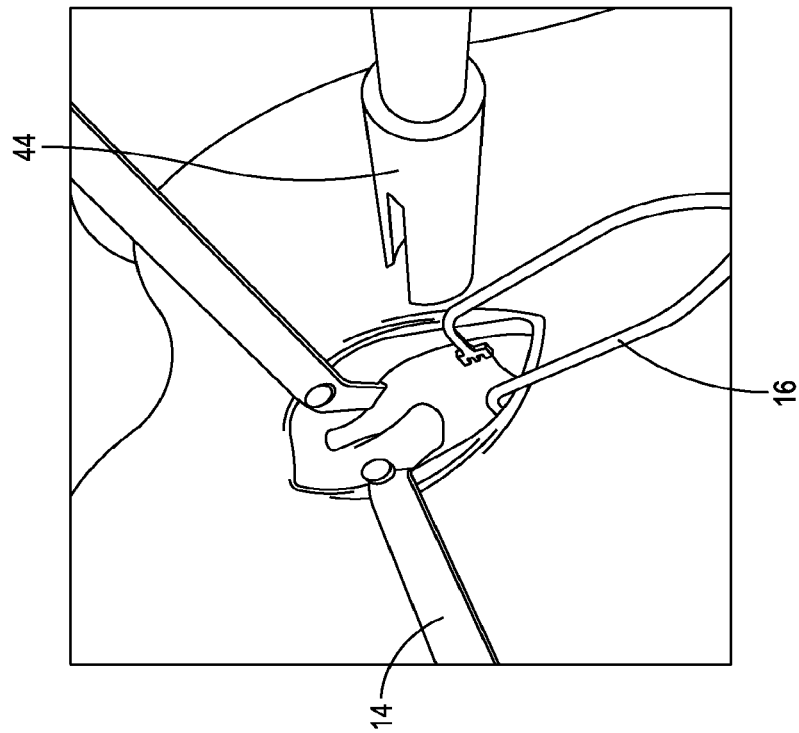

Referring to FIG. 21, to allow for easier insertion of the femoral broaches subsequently, an appropriately sized round calcar punch 44 (e.g., P/Ns 20070052, 20070053 and 20070054) and impactor handle (e.g., P/N 8000010) are utilized in some embodiments. In some embodiments, a round box cutter osteotome 60 can be also used as described in FIG. 29. By opening the neck and starting at the reamer opening, a slot can be created toward the acetabular rim. Additional adduction pressure can be applied to maximize the exposure.

Figure 22:
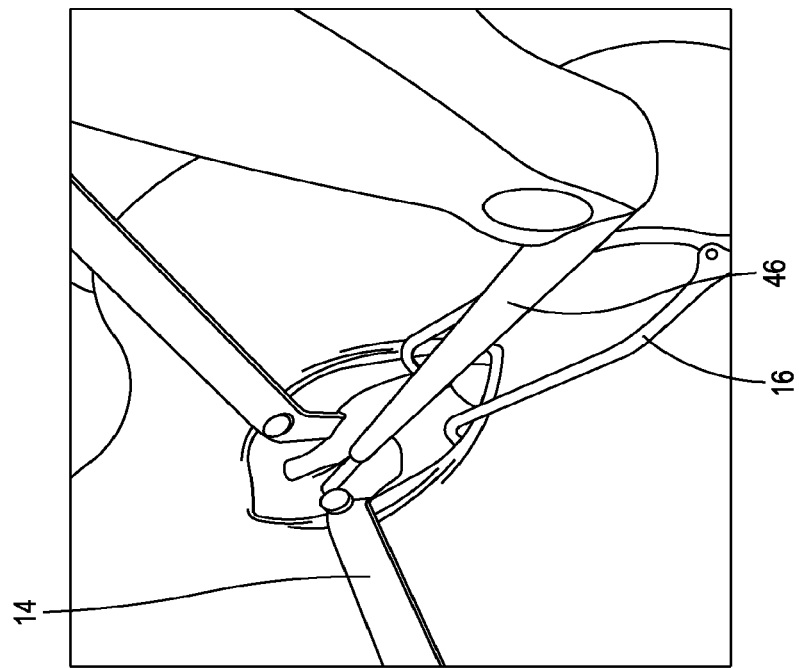

Referring to FIG. 22, a calcar curette 46 (e.g., P/N 20071006) is then introduced into the femur 10 to prepare the proximal-medial portion of the canal, making sure the surface provides good cortical contact to promote bone on-growth while preventing subsidence and micromotion.

Figure 29:
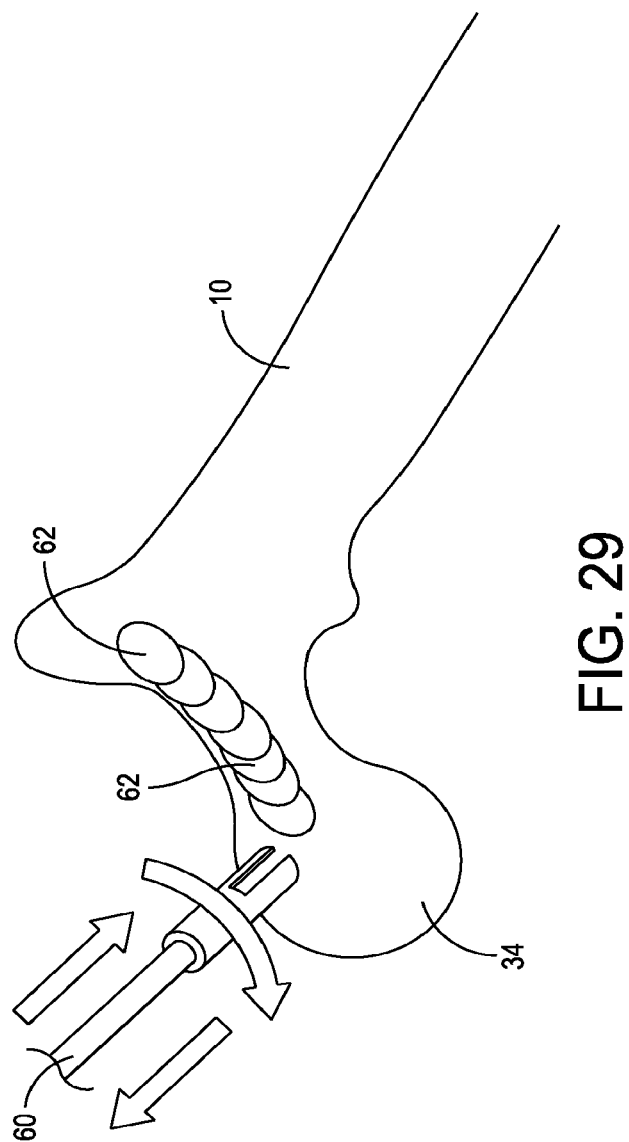
FIG. 29 illustrates an exemplary method of cutting and removing bone fragments during the step of preparation of femur in some embodiments.

Referring back to FIG. 21 and forward to FIG. 29, an exemplary method of cutting and removing bone fragments can be used during the step of femur preparation in some embodiments. The round box cutter osteotome 60 can be a round calcar punch 44, or a modified variation, and has a lower end of cylindrical shape with an opening on the wall parallel to the central axis. As illustrated in FIG. 29, the round box cutter osteotome 60, which is coupled with a spinning tool (not shown), is configured to cut the bone when it spins in one direction, while removing the bone fragments simultaneously. The bone fragments are removed through the opening on the wall. In some embodiments, a "walking canoe" is prepared by forming a hole from the initial starting reamer hole 62 (on the right side as shown in FIG. 29) at the end of femur 10 to the center of femoral head 34. The round box cutter osteotome 60 is very efficient for rapid and precise preparation of femur in-situ with bone fragment removal. In addition, the round box cutter osteotome 60 can be repeatedly used during the surgery without the need of extensive cleaning.

(6) Femoral Broaching

Figure 24:
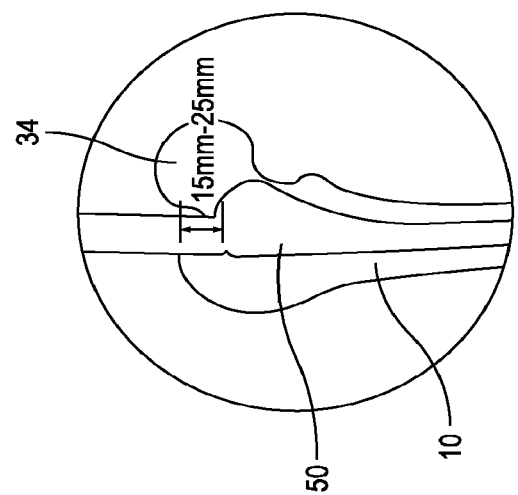
FIGS. 23-24 illustrate a step of femoral broaching in some embodiments.
Figure 23:
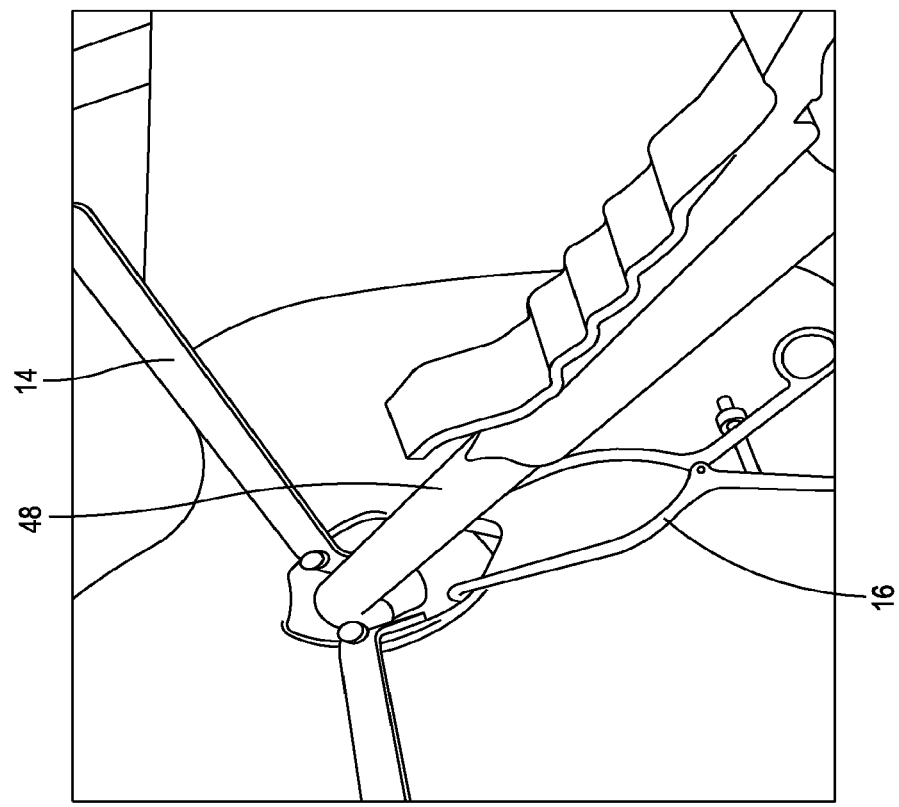

Referring to FIGS. 23-24, a step of femoral broaching is performed in some embodiments. FIG. 24 is an enlarged sectional view of a portion of FIG. 23 illustrating the location of broaches 50 in the femur 10 having femoral head 34. Femoral broaching, also a step of femoral preparation, is performed by placing a femoral broach in the femoral canal for use as a template.

To prepare the femoral canal, broaches 50 can be utilized according to the appropriate ream-and-broach or broach-only stem selected. A slotted broach handle 48 (e.g., P/N SLBROHAN) includes measurement markings to facilitate in the determination of the depth of the top of the broach with regards to the tip of the greater trochanter. The depth is typically 15-25 mm and varies depending on patient anatomy and preoperative leg length discrepancy and can also be checked using a canal feeler (e.g., P/N 20071008). Once the final broach 50 is seated, the broach handle 48 is removed and the broach 50 is used as an internal neck cutting guide. Broach 50 is removed subsequently before the hip replacement parts are implanted.

The methods and the tools related to broaching are also described in U.S. Pat. No. 7,105,028, which is incorporated herein by reference in its entirety.

(7) Femoral Head Resection

Referring to FIG. 25, a step of resecting femoral head 34 is performed in some embodiments. To bring the plane of the femoral neck osteotomy in-line with the surgical wound, an assistant can help to lift the knee in slight hip abduction. A saw 52 such as an oscillating saw with a narrow blade is used to create the femoral neck osteotomy along the top of the broach 50 (P/N PLSB0015, for example). The anterior and posterior sections of the cut are completed using another saw 52 such as a reciprocating saw.

Referring to FIGS. 26-28, exemplary tools and an exemplary method are used to measure the femoral head 34 before resecting the femoral head 34 in accordance with some embodiments. The exemplary method is a method of head-center offset measurement for in-situ total hip arthroplasty (THA). FIG. 26 is a perspective view of a measuring tool 54 and a short modular neck 56 in a femoral head 34 having a broach 50. FIG. 27 is a sectional view of the measuring tool 54 inserted into the broach 50 or an implant 56 inside the femoral head 34. FIG. 28 is a top-down view of the set-up of FIG. 27.

In some embodiments, the measuring tool 54 is a "back hook" trial cup remover used to remove a trial cup in subsequent procedures. The measuring tool 54 can be also a modified "back hook" trial cup remover. The measuring tool 54 has a lower end near the tip. The length of the lower end x as shown in FIG. 26 is configured to have about the same as the distance (x') from the center of rotation in the femoral head and the top surface of an implant 56 such as a short profemur modular neck as shown in FIG. 26. The distance is the sum of the length of the implant 56 and additional femoral offset (y) of implant relative to native femur. The modular neck as an implant 56 can be inserted into the broach 50 in some embodiments.

As shown in FIGS. 27-28, the measuring tool 54 (e.g., a back hook trial cup removal or a modified variation) can be inserted into the broach 50 or an implant 56 inside the femoral head 34 to measure the center of rotation of the broach 50 or the implant 56, and the additional femoral offset (y) of implant relative to native femur. In some embodiments, the measuring tool 54 can be modified to match with any implant or any sizing, including nonmodular stems.

(8) Femoral Head Removal

Figure 30:
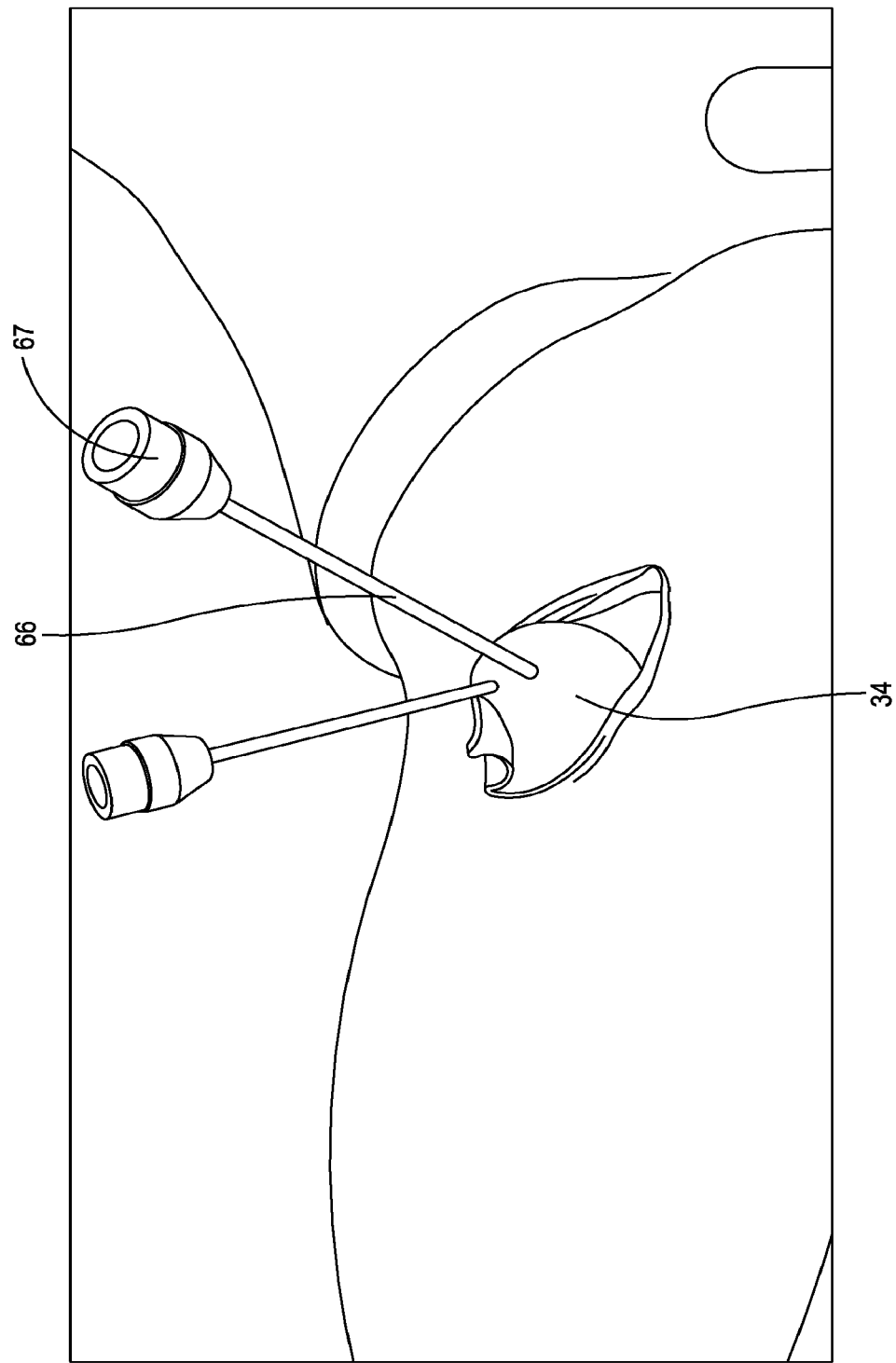
FIG. 30 illustrates a step of femoral head removal in some embodiments.

Referring to FIG. 30, a step of femoral head removal is performed in some embodiments. A first Schanz pin 66 (e.g., P/N 20070057) is inserted into a solid part of the femoral head 34, and the first Schanz pin 66 is levered to rotate the femoral head 34 into maximum adduction. A Schanz pin 66 can be coupled with a handle 67. A second Schanz pin 66 is then placed into another solid part of the femoral head 34 and, using the drill chucks still attached, the femoral head 34 is pulled from the main incision. Should the head be difficult to extract, the first Schanz pin 66 can be removed and the femoral head 34 rotated further into adduction before inserting another pin. The femoral head 34 can continually be "walked" into maximal adduction until the ligamentum teres 70 is either torn or is presented so that it may be severed with electrocautery.

Figure 31:
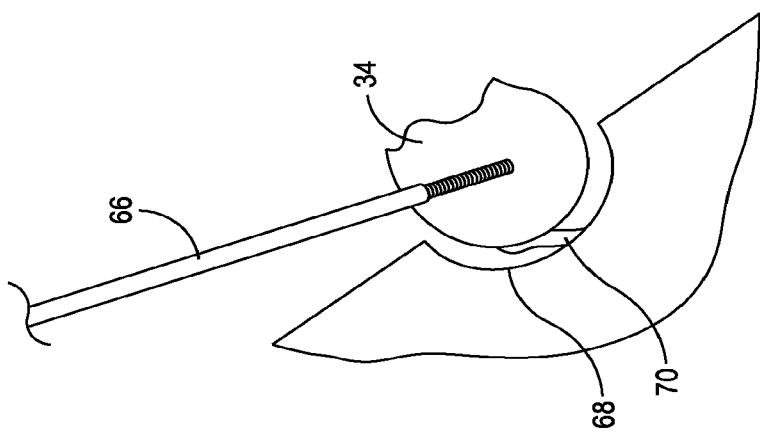

An exemplary method of removing the femoral head 34 is illustrated in details in FIGS. 31-35 in accordance with some embodiments. This method is also referred as "Shantz pin walking" technique. Referring to FIG. 31, the femoral head 34 is located inside the acetabulum 68 and connected with the acetabulum 68 through ligamentum teres 70. The first Schanz pin 66 is inserted into a solid part of the femoral head 34. The first Schanz pin 66 can be used to rotate the femoral head 34 into maximum adduction.

Figure 32:
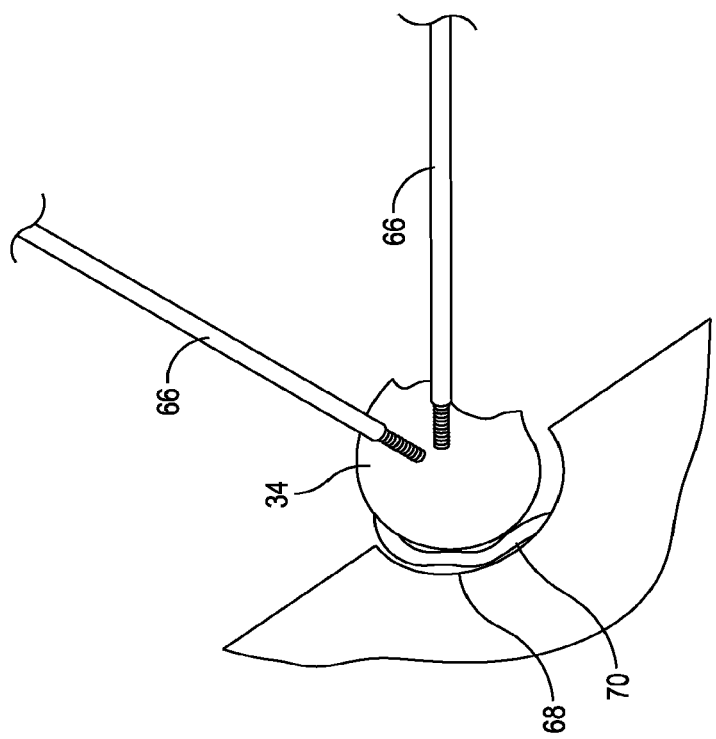
FIGS. 31-35 are sectional views illustrating a method of removing the femoral head in accordance with some embodiments.

Referring to FIG. 32, a second Schanz pin 66 is then placed into another solid part (a different solid part) of the femoral head 34. The ligamentum teres 70 may be stretched at this stage. In some embodiments, the first Schanz pin 66 can be removed before inserting the second Schanz pin 66.

Figure 33:
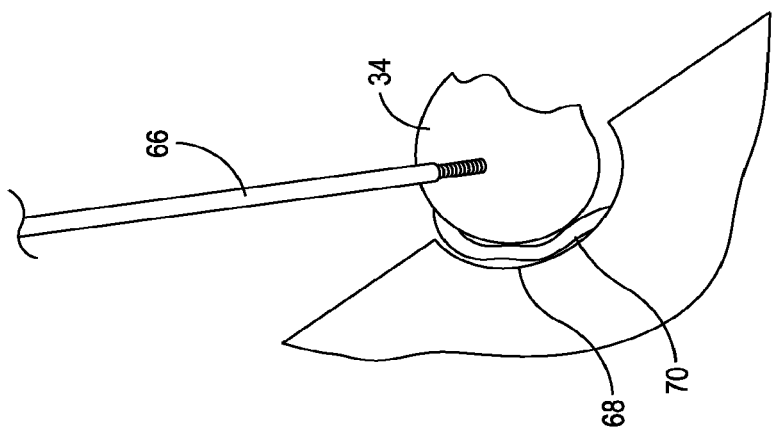

Referring to FIG. 33, the second Schanz pin 66 can be used to rotate the femoral head 34 into maximum adduction.

Figure 34:
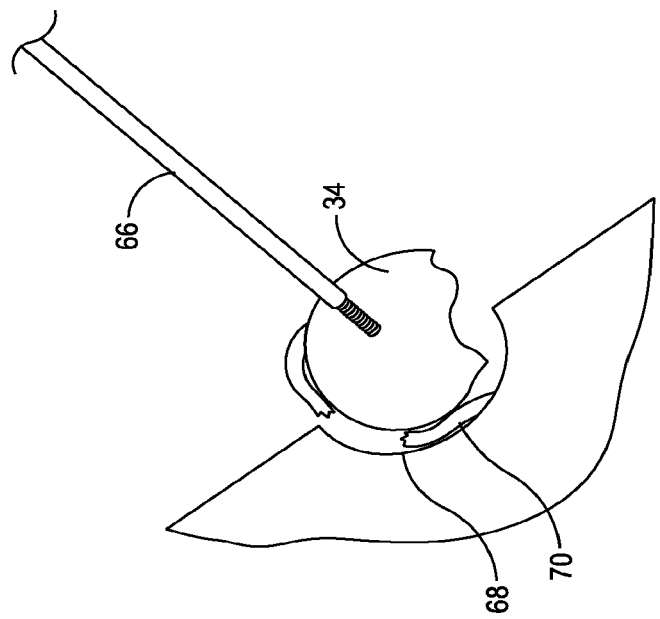

Refereeing to FIG. 34, when the second Schanz pin 66 can be used to rotate the femoral head 34, the ligamentum teres 70 may be torn, exposed, or removed from the acetabulum 68. The ligamentum teres 70 outside the acetabulum 68 can be directly dissected in some embodiments.

Figure 35:
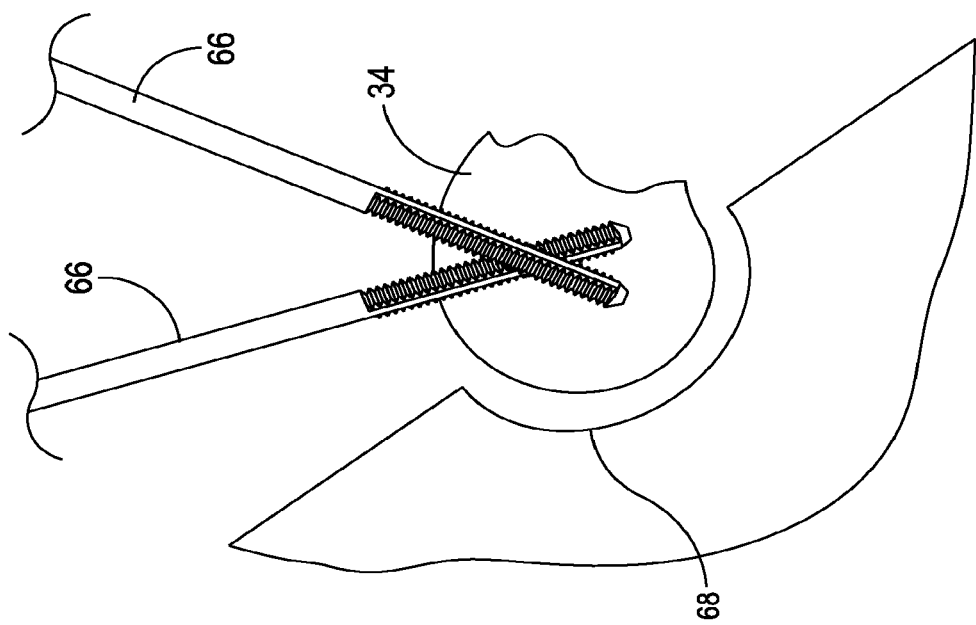

Referring to FIG. 35, the first Schanz pin 66 can be inserted to another solid portion of the femoral head 34. The two Schanz pins 66 can point to different directions. This cross-pin fixation can be used for extraction of the femoral head in situ total hip arthroplasty (THA). As shown in FIG. 35, in some embodiments, the pins 66 used have cross threads in the tips for better fixation and removal.

The pins 66 and the related techniques for the femoral head removal are for the illustration purpose only. The pins 66 and the related techniques described can be applied to any type of bones including bone fractures. The fixation/removal can be done with streamlining and less expensive tooling.

(9) Acetabular Preparation

Figure 36:
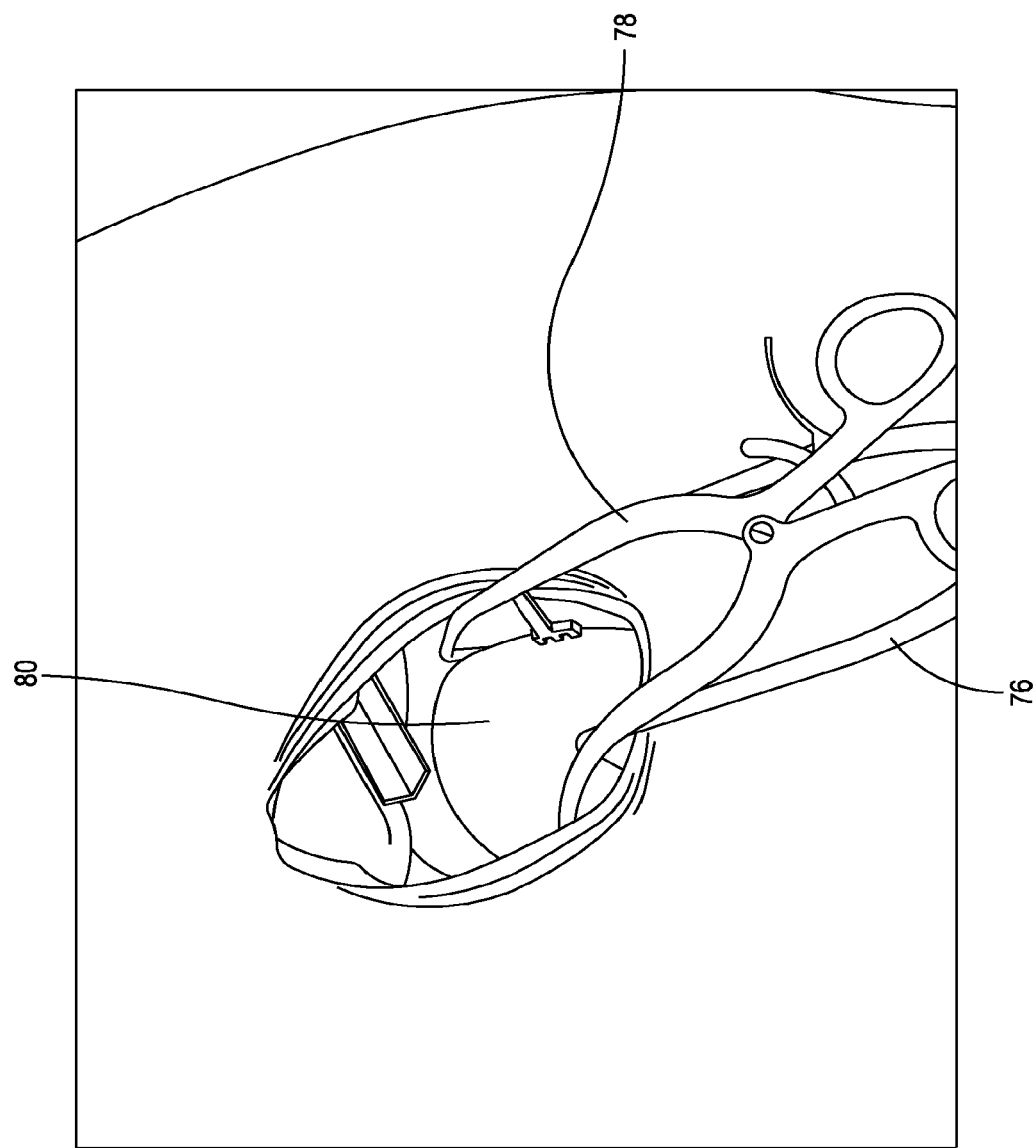
FIG. 36 illustrates a step of acetabular preparation in some embodiments.

Referring to FIG. 36, a step of acetabular preparation is performed in some embodiments. With the leg in the "home position," two spiked Hohmann retractors (e.g., P/N 20073113, not shown) are placed into the axilla between the capsule and the labrum on both the front and back sides of the acetabulum 68. Under direct visualization, any remaining tissue is removed from the acetabulum 68, as well as the labrum, to expose the surface and volume 80 of the acetabulum 68. The obturator artery is often encountered posteriorly. After removal of soft tissue, bleeding can be controlled using electrocautery (a long tip is recommended).

A Zelpi retractor 76 (e.g., P/N 20071004) or a modified variation is placed subperiosteally at the acetabular margin at the proximal incision, and a Romanelli retractor 78 (e.g., P/N 20071001) immediately distal intra-articularly. The combination of these self-retaining retractors 76 and 78 will provide rotational stability, as well as create a surface on which to introduce the reamers and the implant into the joint. The spiked Hohmann retractors are now removed.

Figure 37:
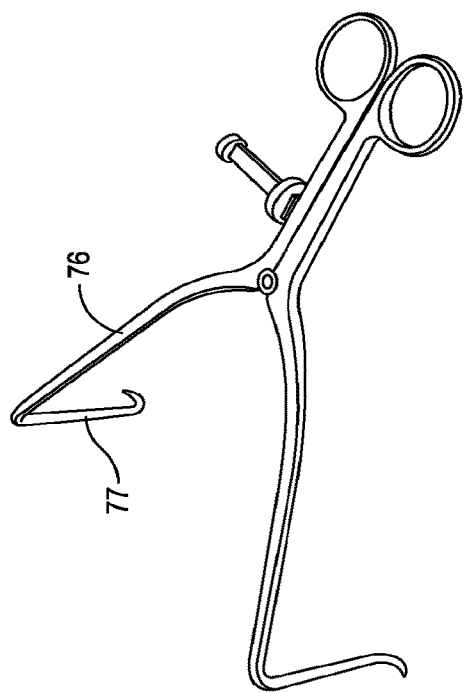
FIGS. 37-39 illustrate a modified Zelpi retractor having tines in accordance with some embodiments.
Figure 39:
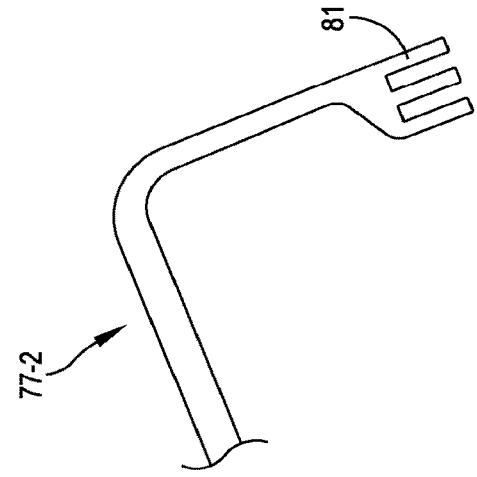
Figure 38:
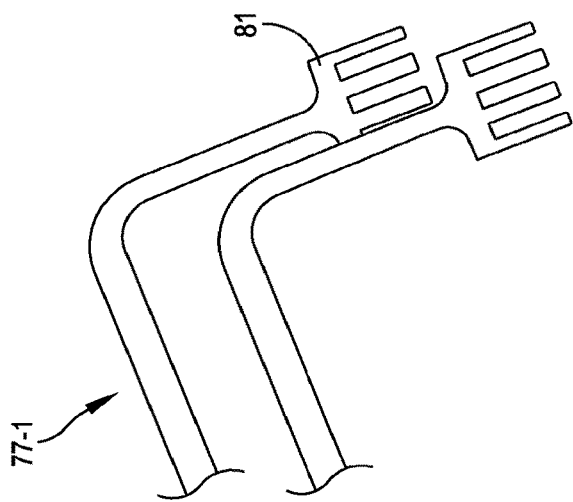

Referring to FIGS. 37-39, the inventor has designed a series of new Zelpi retractor 76 having tines 81 in accordance with some embodiments. FIG. 37 illustrates a Zelpi retractor 76 having two tip rails 77. Referring to FIG. 38, in some embodiments, each tip rail 77-1 has a plurality of tines 81 symmetrically distributed on both sides along the tip rail 77-1. Referring to FIG. 39, in some other embodiments, the tip rails 77-2 are straight to the end. Tip rail 77-2 has tines 81 only on one side of the tip rail 77-2. In some embodiments, the tines 81 in either tip rail 77-1 or 77-2 are substantially parallel to each other and to the respective tip rail. The inventive Zelpi retractor 76 provided in the present disclosure can have tip rail type 77-1 or 77-2 with the tines 81 described, or any combinations thereof. The inventive Zelpi retractor 76 having tines can facilitate subsequent insertion of an acetabular cup, and also provide unencumbered access to the acetabulum 68.

Figure 40:
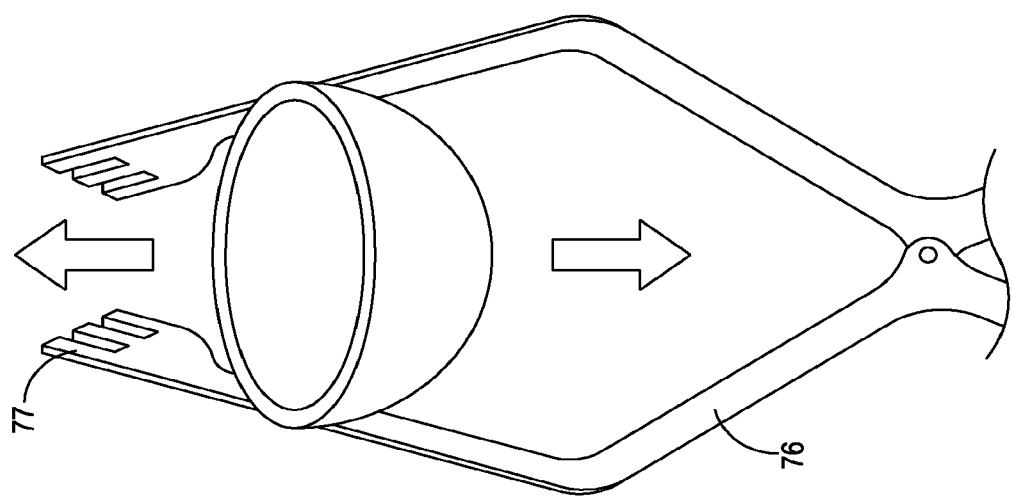
Figure 41:
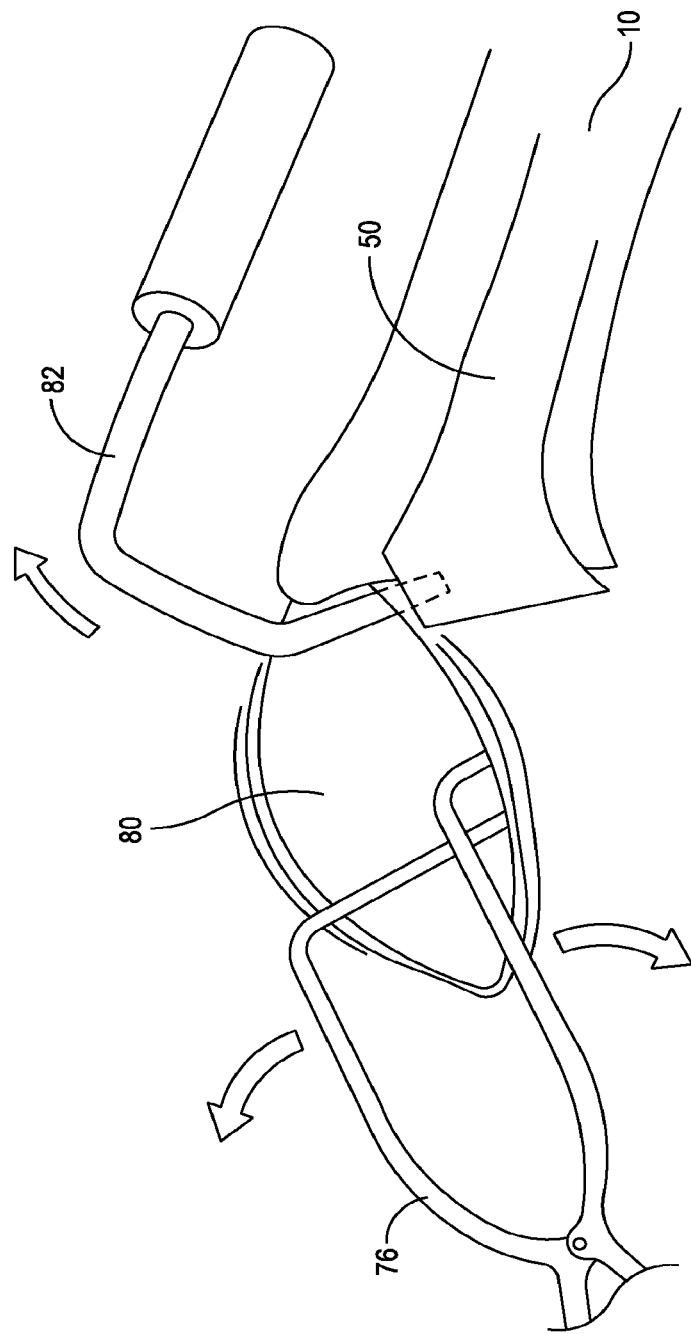

Referring to FIGS. 40-42, the modified Zelpi retractors 76 shown in FIGS. 37-39 can be used to facilitate the surgery. FIG. 40 is a top down view of a modified Zelpi retractor 76 being used. As shown in FIG. 40, the modified Zelpi retractor 76 having tines can be used to create an open space to show the acetabulum 68 with its surface/volume 80. The modified Zelpi retractor 76 can be moved by sliding along soft tissues only to create a different open space (a mobile window) to facilitate subsequent insertion of an acetabular cup. Additionally, the modified Zelpi retractor 76 having tines has two arms. Each arm is at an angle (such as 90 degree) to a respective tip rail 77-1 or 77-2. The modified Zelpi retractor 76 creates or functions as a "railway" to hold and move the acetabular cup or other parts such as a reamer basket, for example, into the acetabulum of the femur.

FIG. 41 is a side view and FIG. 42 is a top down view of a modified Zelpi retractor 76 being used in combination with other tools such as a bone hook 82, which is placed in the broach 50 inside and along the femur 10. In all the traditional hip replacement techniques, bone retraction is used. As described, by retracting soft tissues only, the modified Zelpi retractor 76 in the present disclosure can be used to create a mobile window (over the existing capsule), including the surface/volume of the exposed acetabulum 68. By moving retraction along or to the soft tissue, better exposed is achieved with less dissection by the method of creating a mobile window. The retractors are not fixed to stationary bony structures. The existing capsule can be used to further aid retraction. As shown in FIG. 42, with the aid of bone hook 82, a three-point capsular distraction is achieved. The bone hook and the two tip rails are configured to form the three-point capsular distraction. The bone hook 82 placed in broach 50 allows distraction without force directly on any bone including the femur 10. The three-point capsular distraction provides maximum protection to muscles, nerves, and vessels. Overall, by using the modified Zelpi retractor 76 having tines, a minimally invasive hip replacement is achieved. The incision is easily sealed and easily heals.

(10) Percutaneous Incision Placement

Figure 44:
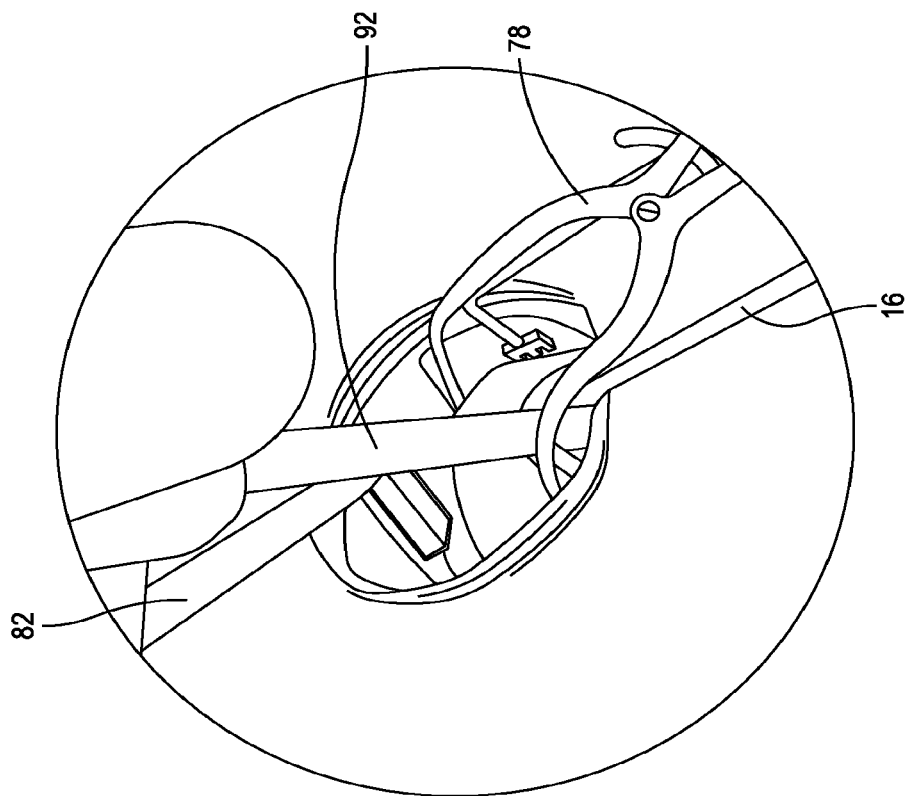
FIGS. 43-44 illustrate a step of percutaneous incision placement in some embodiments.
Figure 43:
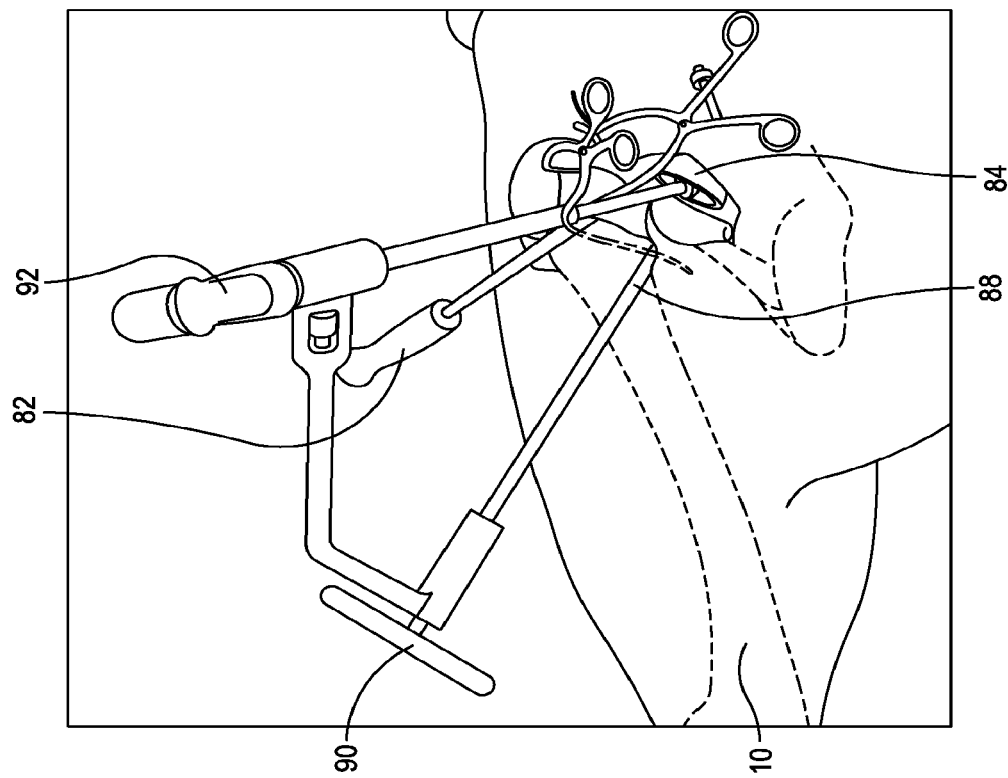
Figure 45:
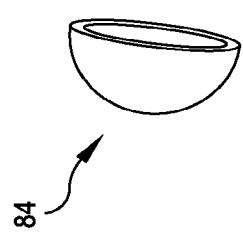
FIGS. 45-47 illustrate exemplary tools used in the step of FIGS. 43-44 in some embodiments.
Figure 47:
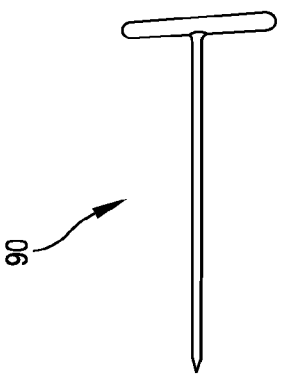
Figure 46:
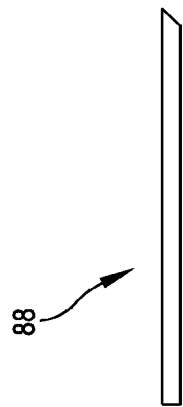

Referring to FIGS. 43-44, a step of percutaneous incision placement is performed in some embodiments. The exemplary tools shown in FIGS. 45-48 are for the illustration purpose only.

With the leg still in the "home position," have an assistant insert the tip of the bone hook 82 (e.g., P/N 20071011) into the top of the broach 50 and retract the femur 10 anteriorly. An assembly 92 comprising an alignment handle (e.g., P/N 20071009), a portal placement guide (e.g., P/N 20070015), a threaded cup adapter (e.g., P/N 20070013) and a trial cup 84 (e.g., P/N 20070146, shown in FIG. 45), is seated in the acetabulum 68 with the top of the guide perpendicular to the patient's torso, and the guide shaft tilted 10°-15° from vertical to account for the pelvic tilt of the patient on the table. The methods and the tools related to using an assembly comprising an alignment handle are also described in U.S. Pat. No. 7,651,501, which is incorporated herein by reference in its entirety.

A blunt Trocar 90 (e.g., P/N 20070116, FIG. 47) with a cannula 88 (e.g., P/N 2007ST20, FIG. 46) is inserted until resting against the operative leg. At the point where the blunt Trocar 90 intersects the leg, a 1cm stab incision (a portal incision) is made horizontally. The blunt Trocar 90 and the cannula 88 are then passed through the stab incision and 1-2 cm posterior to the femur 10 until they are visible through the main incision. The assembly 92 of alignment handle/portal placement guide/threaded cup adapter/trial cup and blunt Trocar 90 are then removed, leaving the cannula 88 in place. The cannula 88 can be easily moved for directional reaming by positioning the leg.

The methods and the tools related to using a cannula are also described in U.S. Pat. No. 6,997,928, which is incorporated herein by reference in its entirety.

(11) Acetabular Reaming

Figure 49:
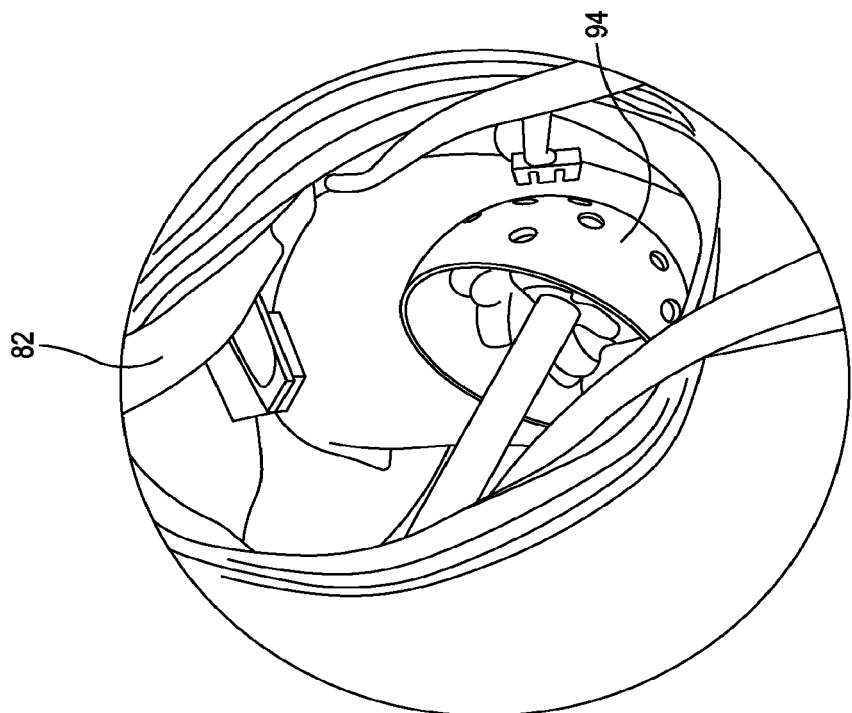
FIGS. 48-49 illustrate a step of acetabular reaming in some embodiments.
Figure 48:
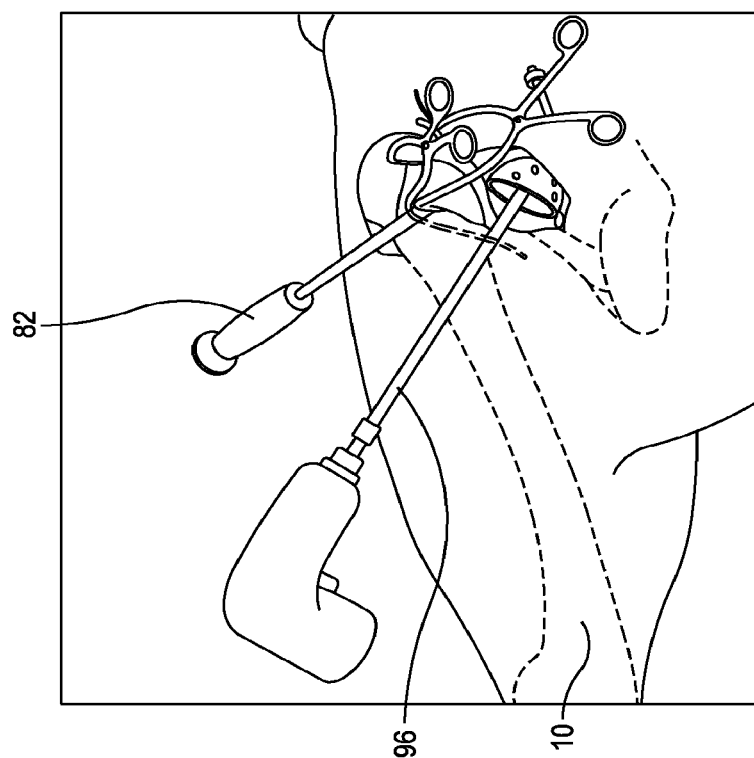

Referring to FIGS. 48-49, a step of acetabular reaming is performed in some embodiments. FIG. 49 is an enlarged view of a portion of FIG. 48. An appropriately-sized reamer 94 such as a hex acetabular reamer (e.g., P/Ns PATHRM40-PATHRM64) is passed into the main incision using a reamer basket holder 96 (e.g., P/N 20070048). A reamer shaft 97 (e.g., P/N 20070011) is passed through the cannula 88 and mated to the reamer 94 such as the hex acetabular reamer in situ. Acetabular preparation is performed using the preferred reaming method. Medial reaming is often carried out through the main incision prior to deepening/enlarging the acetabulum 68.

Figure 51:
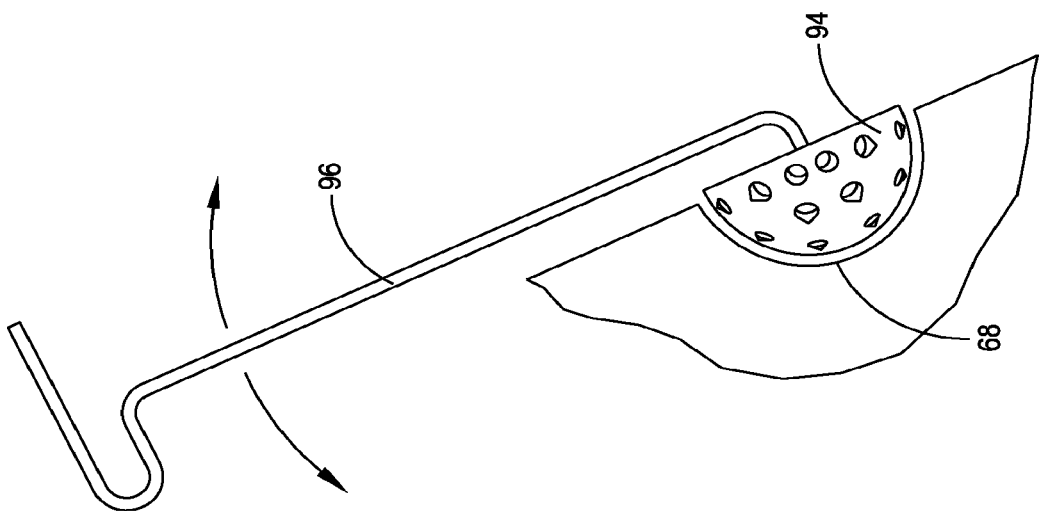
FIGS. 50-51 are sectional views illustrating a method and a tool for placing and removing a reamer basket in accordance with some embodiments.
Figure 50:
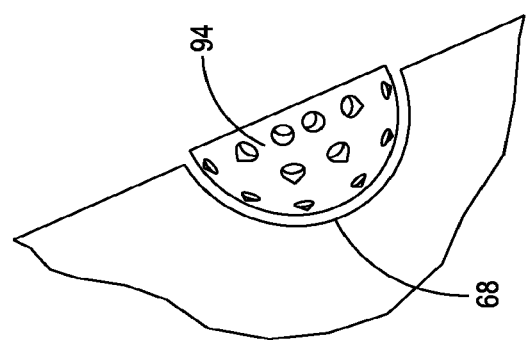

Referring to FIGS. 50-51, an exemplary method with an exemplary tool is used for placing and removing a reamer basket 94 in accordance with some embodiments. As shown in FIG. 50, a reamer basket 94 such as a hex acetabular reamer is placed into the acetabulum 68. In some embodiments, this step is performed using a unique reamer basket holder 96 as shown in FIG. 51. The reamer basket holder 96 provided in the present disclosure comprises a substantially straight main body, a small bent bottom tip and a bigger bent top handle. The small bent bottom tip is at an angle with the main body, or is substantially perpendicular to the main body in some embodiments. The small bent bottom tip has a suitable size and is configured to be inserted into a hole on the reamer basket 94 as shown in FIG. 51. As shown in FIG. 51, the bent top handle can be bent twice. The top handle is configured to be easily grabbed by a hand. The reamer basket holder 96 is configured to rotate the reamer basket 94 around the contacting point after the tip of the reamer basket holder 96 is placed into the reamer basket 94 (FIG. 51).

During the step of acetabular reaming, in some embodiments, the acetabulum 68 can be first reamed using different sized reamers. Second, at one size smaller than final implant size, the reamer basket 94 should display rotational resistance. The reamer basket 94 should remain in the position against its gravity. Third, final implant size is reamed using a limited number of revolutions, and the final implant has a minimal impact to sphericity of acetabular preparation. This method of acetabular reaming does not need to separately have trial cups. With streamlining tooling, it is not necessary to supply extra parts for the trialing steps. The method provides much reduced cost for manufacturing and inventory. The method also provides streamlined operational flow, with much easier procedure, higher surgeon adoption and easier set-up.

(12) Cup Placement

Figure 53:
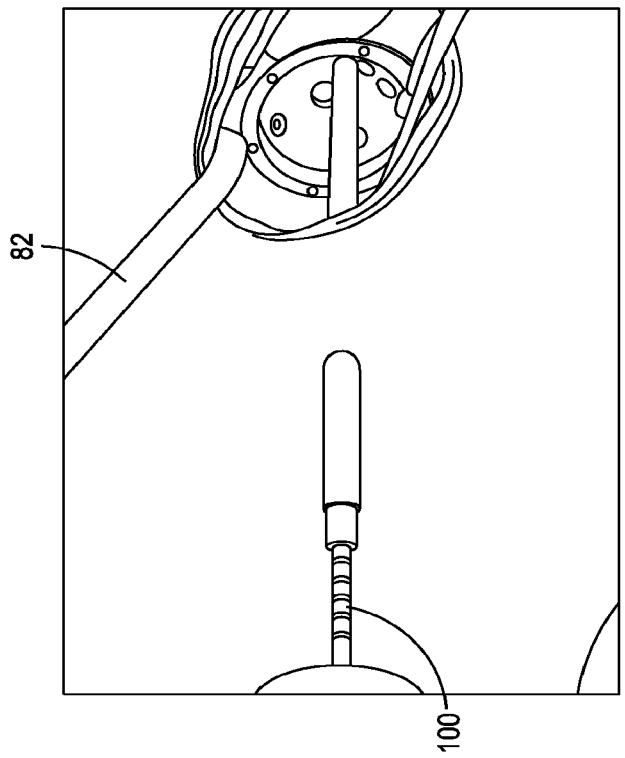
FIGS. 52-53 illustrate a step of cup placement in some embodiments.
Figure 52:
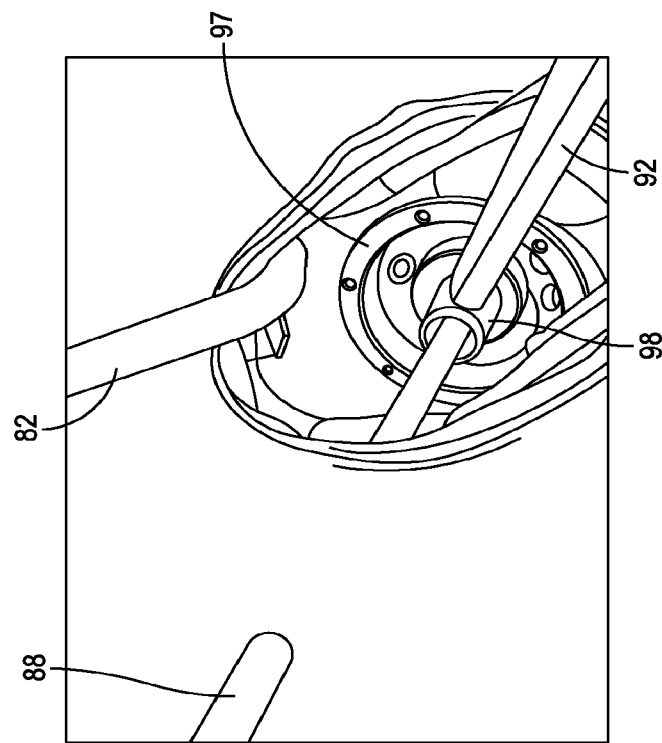

Referring to FIGS. 52-53, a step of cup placement is performed in some embodiments. A threaded cup adapter 98 is threaded into the apical hole of an acetabular cup 97, and an acetabular cup 97 and threaded cup adapter 98 are seated on an assembly comprising an alignment handle 92, as shown in FIG. 52. The alignment handle 92 is designed to provide 25° anteversion when perpendicular to the torso of the patient, and 40° abduction when perpendicular to the floor.

With the acetabular cup 97 in the acetabulum 68, the alignment handle 92 is directly driven to medialize the acetabular cup 97. In some embodiments, a cup impactor (e.g., P/N 20071010) is inserted through the cannula 88 and the tip of the alignment handle 92 until seated in the dimple of the threaded cup adapter 98. With the shaft of the alignment handle 92 again tilted 10°-15° from vertical to account for the pelvic tilt of the patient on the table, the cup impactor is impacted until the acetabular cup 97 is firmly seated. An alignment guide (e.g., P/N 33330080) can be used for attachment on the cup impactor. With the acetabular cup 97 firmly seated, the threaded cup adapter 98 is unscrewed from the acetabular cup 97 using the hex tip of the cup impactor, and removed using a reamer basket holder 96.

Figure 54:
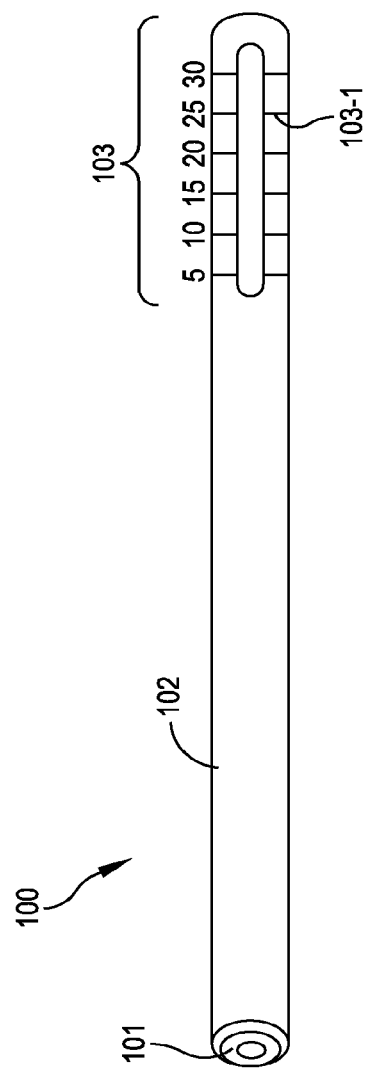
FIGS. 54-55 illustrate a depth gauge in accordance with some embodiments.
Figure 55:
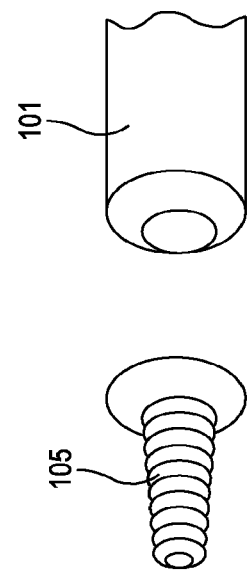
Figure 56:
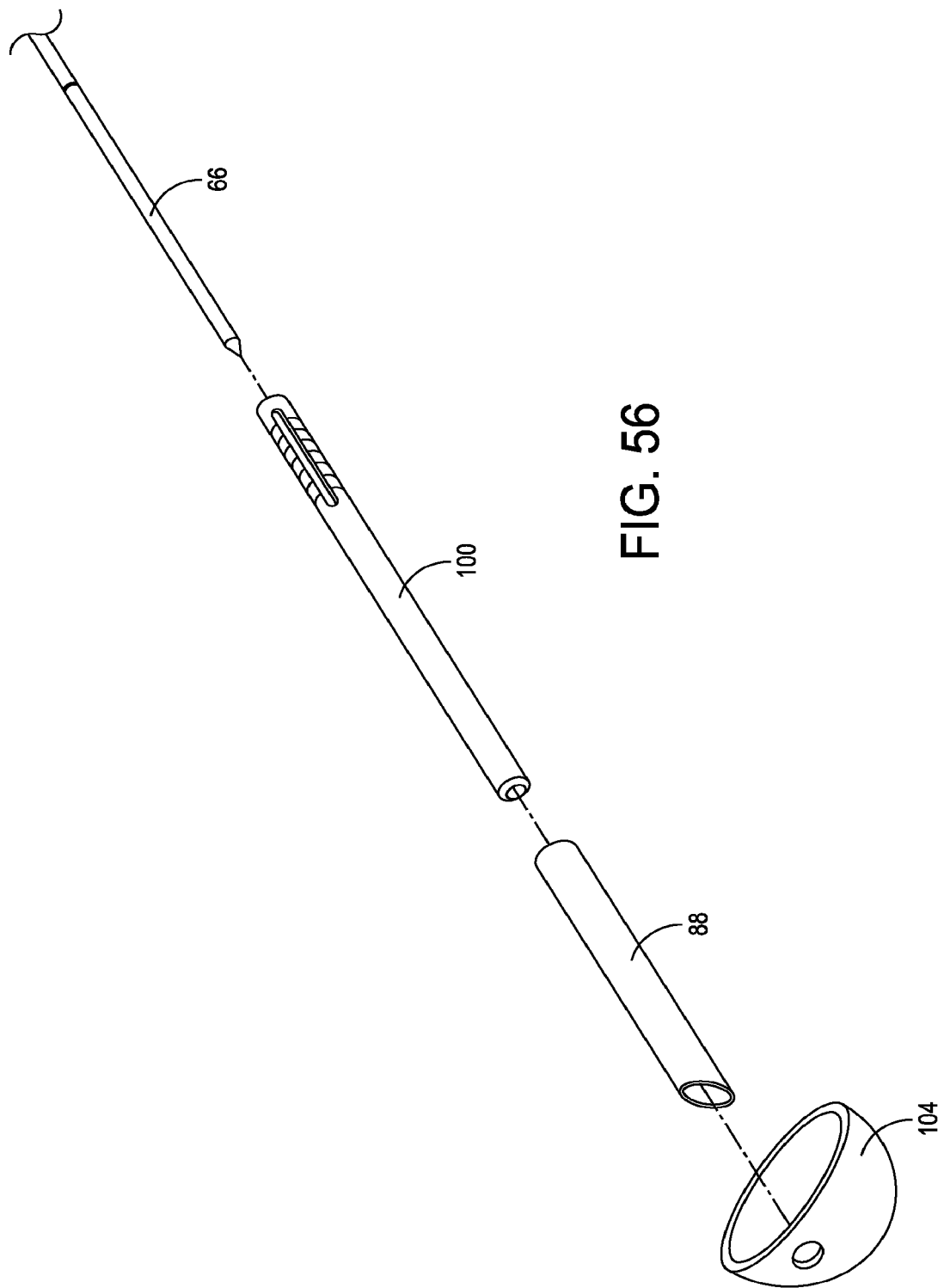

Referring to FIG. 53, in some embodiments, a screw centering tool or a depth gauge 100 is used in this step of placing the acetabular cup 97 or placing the screw as a following step in accordance with some embodiments. An exemplary depth gauge 100 is illustrated in FIGS. 54-55. FIGS. 56-57 illustrate a method of using such a depth gauge 100 in some embodiments. The depth gauge 100 can be used for placing an acetabular cup 97 or any other implant 104.

Referring to FIG. 54, an exemplary depth gauge 100 in accordance with some embodiments includes a straight body 102 having two ends: a first end 101 and a second end 103. In some embodiments, the body 102 has a cylindrical shape, and is hollow throughout the entire depth gauge 100. The end 101 may be a screw head itself, or adapted to be coupled with a screw head or a screw 105. The end 101 may have equivalent screw geometry to a center of a hole thereon. In some embodiments, the end 101 has a geometry the same as that of screw head or a screw 105, and is configured to allow centered placement in a hole, which may be for pre-drilling assessment of screw head position and seating.

As shown in FIG. 54, the end 103 in the exemplary depth gauge 100 has graduation or depth marks 103-1. Referring to FIG. 56, in some embodiments, the depth gauge 100 has a suitable inner diameter, and is configured to be inserted into (or pass through) a cannula 88. The depth gauge 100 is so configured that a schanz pin 66 (as described above) can be inserted into or pass through the depth gauge 100. In another word, the inner diameter of the depth gauge 100 is bigger than an outer diameter of the schanz pin 66, and the outer diameter of the depth gauge 100 is small than that of an inner diameter of the cannula 88.

As shown in FIGS. 56-57, the depth gauge 100 is inserted into the cannula 88, which is coupled with an implant 104 (or an acetabular cup 97) through a hole. The schanz pin 66 is inserted into the depth gauge 100. The depth marks 103-1 are configured to indicate and control the depth of insertion of a pin such as the schanz pin 66. The assembled structure is shown in FIG. 57.

The schanz pin 66 is described here for illustration purpose only. Instead of a schanz pin 66, a drill 106 can be used in combination with the depth gauge 100 in some embodiments. In addition, as shown in FIG. 58, instead of having the depth marks 103-1 on one end of the depth gauge 100, a drill 106 or the schanz pin 66 can have the depth marks 107, and is used in combination with one gauge 108 without depth marks, or the depth gauge 100.

(13) Screw Placement

In some embodiments, a screw is placed into the acetabular cup through a pilot hole. The pilot hole can be drilled to a predetermined depth with the aid of a depth gauge for example the depth gauge 100. In some embodiments, pilot holes for the placement of acetabular screws are created by inserting a long drill tube (e.g., P/N 20071012) through the cannula 88 until it engages the desired hole in the acetabular cup 97. A screw drill (e.g., P/N 20071007) is then passed through the long drill tube. Using the measurement markings on the end of the screw drill, drilling is carried out to the desired depth. The screw drill and long drill tube are removed. Additionally, pilot holes can be created in a similar fashion using a drill tube (e.g., P/N 20071005) and a schanz pin. When using this combination, the schanz pin is advanced until bottoming on the drill tube. With continued revolutions of the pin, the threaded bone is stripped and a hole with a depth of 30 mm is created. In some embodiments, the screw drill (e.g., P/N 20071007) is only to be used with the long drill tube (e.g., P/N 20071012) and is not to be used with the drill tube (P/N 20071005) as the depth dimensions will not be accurate.

Screws can be held in position using a set of screw holding forceps (e.g., P/N 4820SH0000) through the main incision, and a ball joint screwdriver (e.g., P/N 20071002) or straight screwdriver (e.g., P/N 20071003) is attached to a ratchet screwdriver handle (e.g., P/N 2002QCRH) and passed through the cannula 88 to engage and tighten the screw(s).

(14) Trial Reduction

Figure 59:
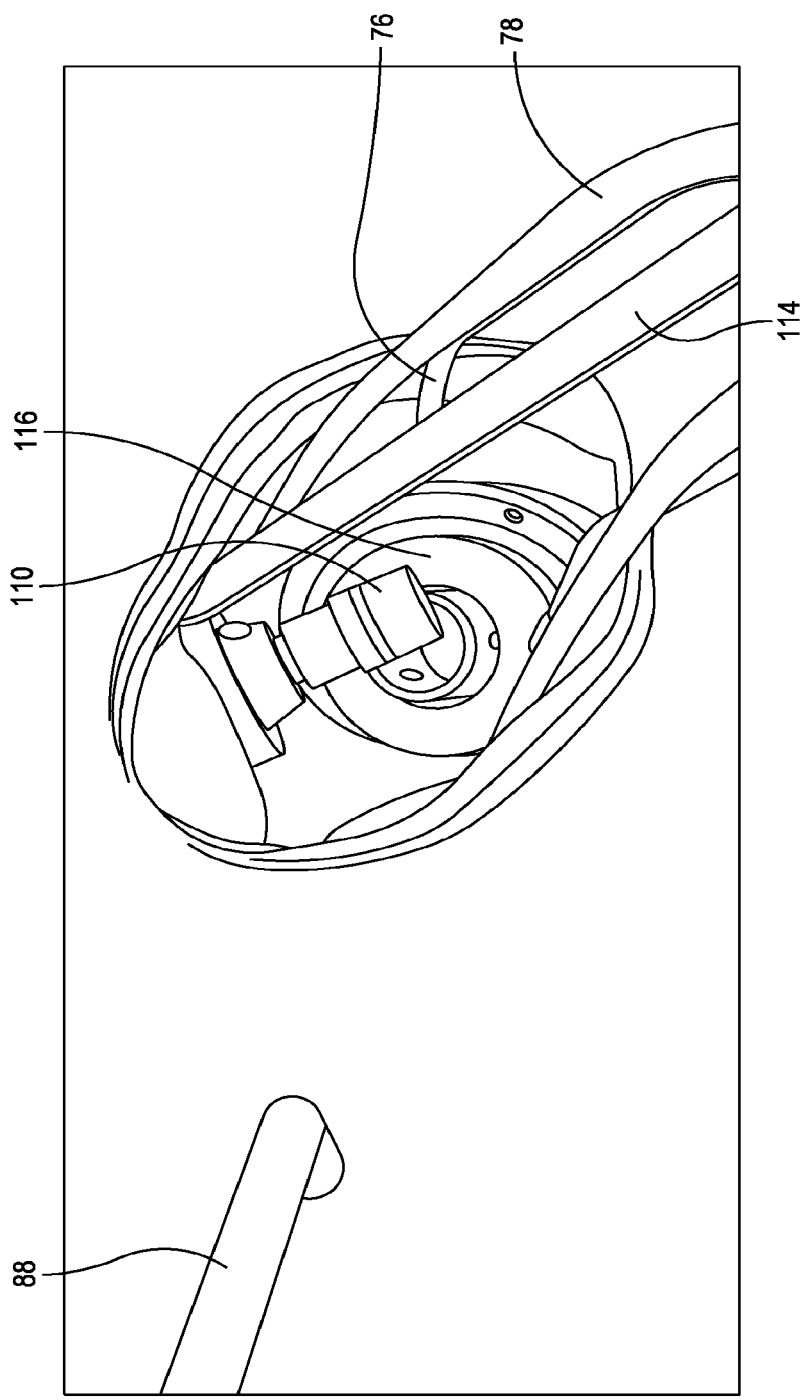
FIG. 59 illustrates a step of trial reduction in some embodiments.

Referring to FIG. 59, a step of trial reduction is performed in some embodiments. Trials of femoral neck 110 and femoral head 116 are chosen by measuring the bone resection or using the components identified during pre-operative templating. For example, a PROFEMUR® Metal Trial Neck (e.g., P/Ns APA12102-APA12154) is placed into the seated broach while controlling the leg position. A set of forceps with angled tips can be used to facilitate this maneuver. A trial head (e.g., P/N APA02121-APA02154, or combination of P/Ns 41102800-41104800 and APA0TSS3-APA0TSL3 if large femoral heads with neck sleeves are used) in the socket and rotate its opening to a superior-posterior position. With the tip of the blunt trocar inserted into the top of the broach 50, mate the trial neck 110 into the trial head 116. During this maneuver, the surgeon controls the leg by pushing and translating the hip under direct visualization through the main incision, while an assistant controls the internal/external rotation of the hip by raising or lowering the foot or knee in some embodiment.

(15) Trial Disassembly

Figure 60:
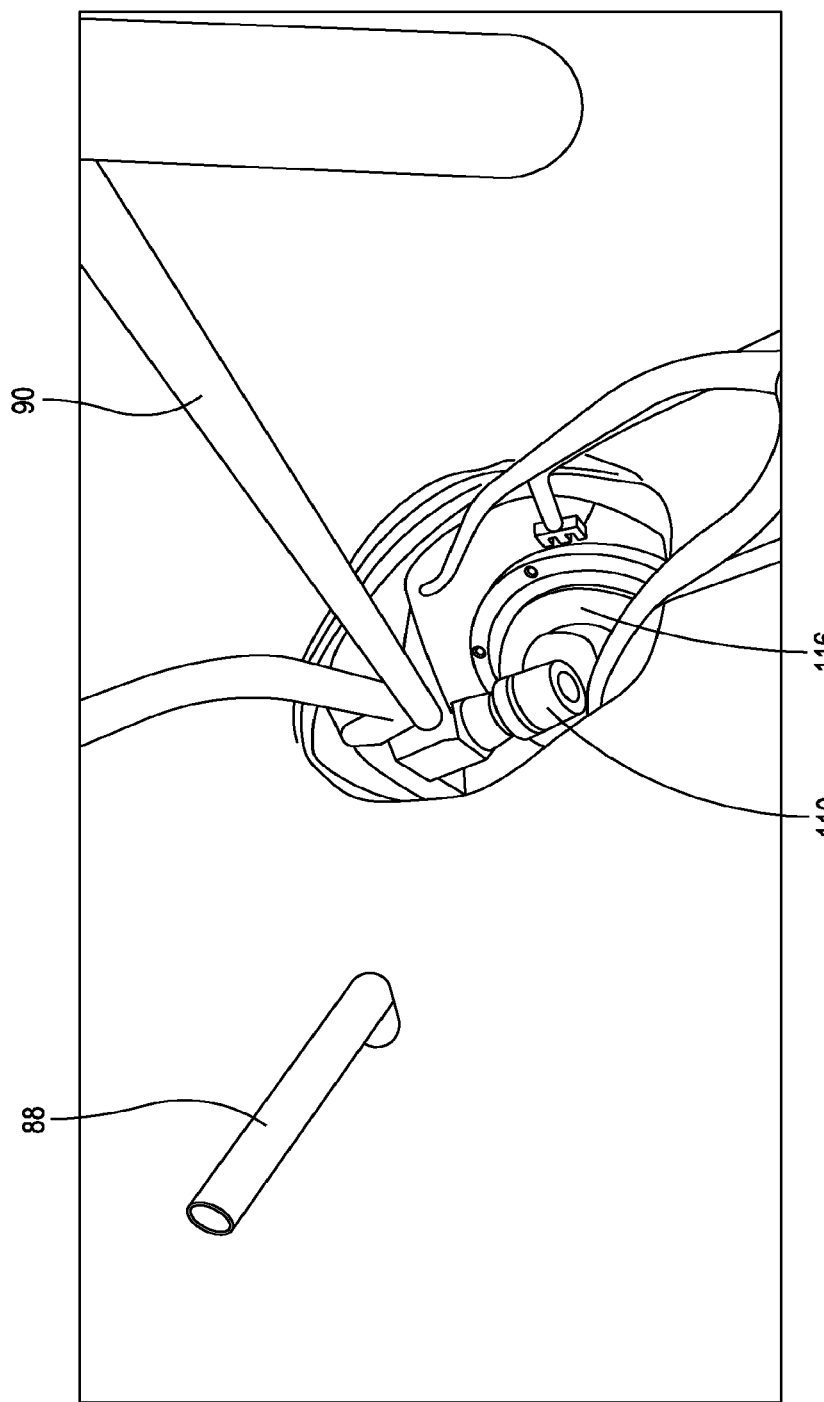
FIG. 60 illustrates a step of trial disassembly in some embodiments.

Referring to FIG. 60, a step of trial disassembly is performed in some embodiments. With the leg in the "home position," an assistant can place the tip of a bone hook 82 or a bone hook tool 120 into the top of the broach 50 and applies lateral traction to the leg. The tip of a blunt trocar 90 is placed into the superior hole in the trial neck 110. By engaging the side of the blunt trocar into the slot near the tip of the bone hook 82 and levering the two instruments against each other, the trial neck 110 is disassembled from the broach 50. The trial components, including the femoral broach 50, are then removed.

Figure 63:
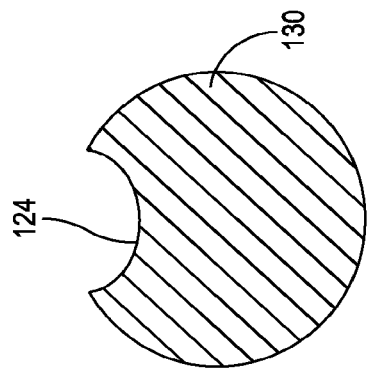
FIGS. 61-63 illustrate a bone hook tool having a indented surface in accordance with some embodiments.
Figure 62:
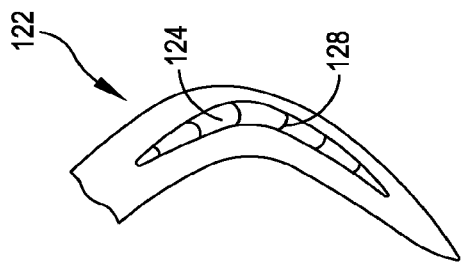
Figure 61:
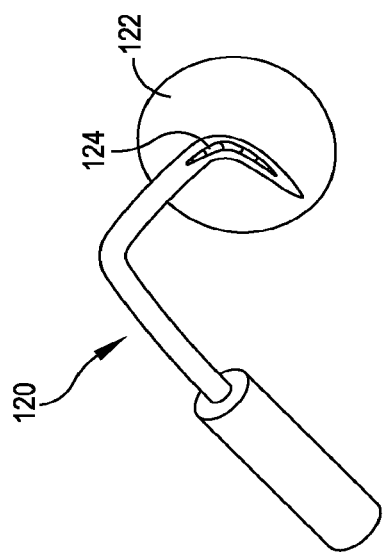
Figure 65:
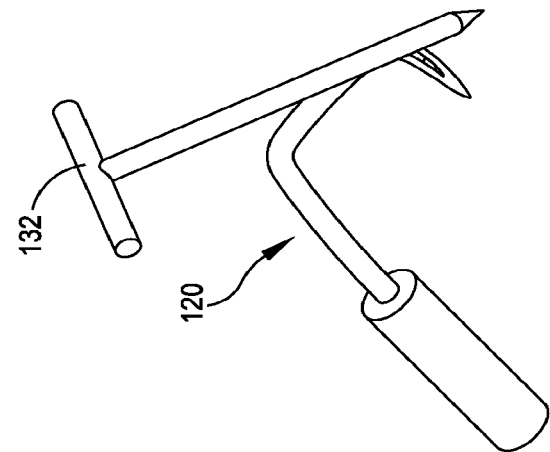
Figure 64:
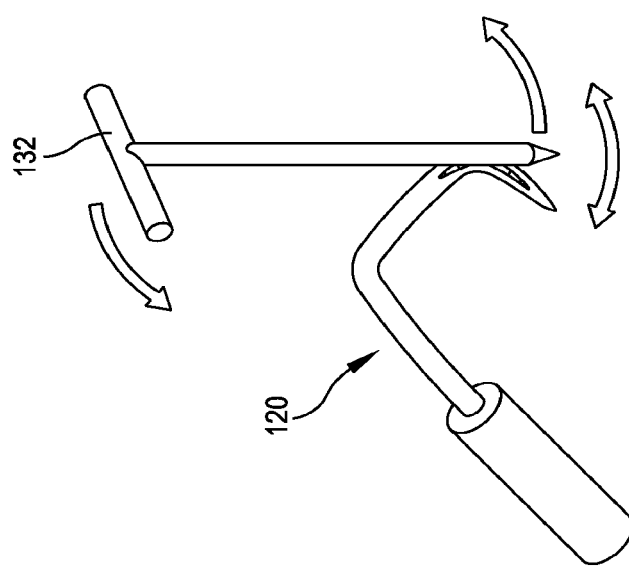
Figure 67:
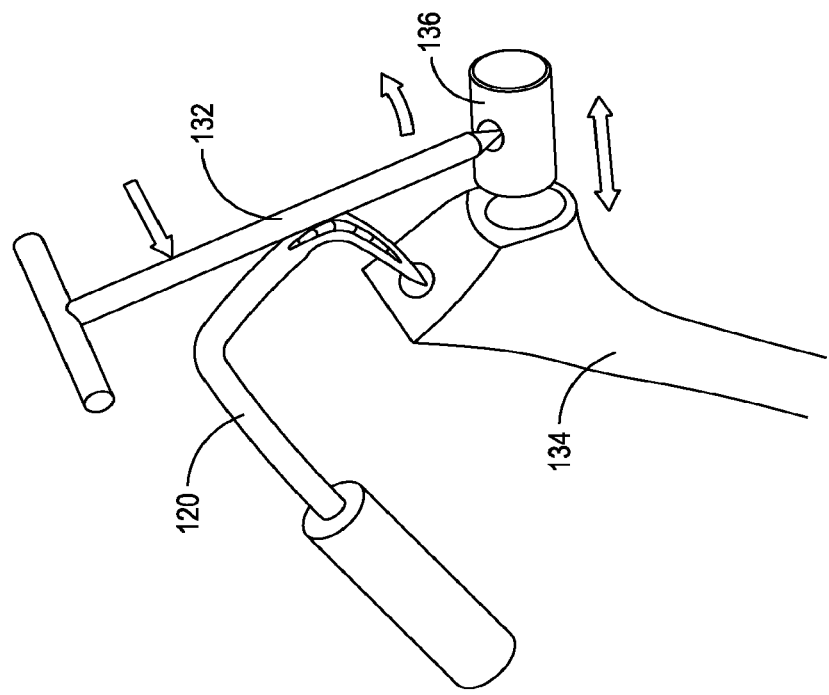
Figure 66:
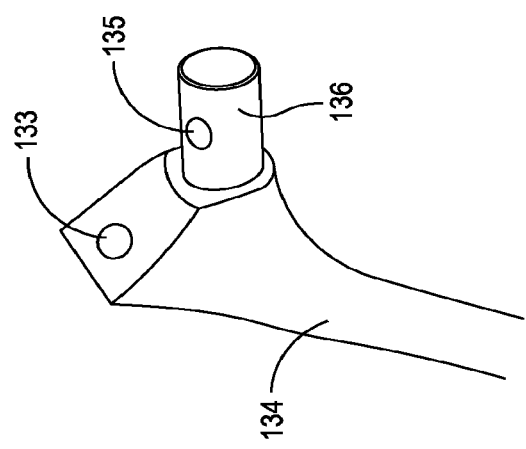

Referring to FIGS. 61-63, a bone hook tool 120 used has a bent tip 122 with an indented surface 124 in accordance with some embodiments. FIG. 62 is an enlarged view of the bent tip 122. FIG. 63 is an enlarged view of the cross section 130 of the bent tip 122. On the outer side of the bent tip 122, the indented surface 124 is configured to be engaged with another tool 132 (FIGS. 64-65) to remove or disassemble a part 136 such as a trial neck 110 without causing any dislocation (FIGS. 66-67). Examples of another tool 132 include but are limited to a blunt trocar 90. In another word, the bent tip 122 has a concaved surface, which is configured to accept a convex surface such as a round surface of the tool 132 such as the blunt trocar 90. The indented surface 124 can be smooth or textured. In some embodiments, the indented surface 124 may optionally have marks 128.

Referring to FIGS. 64-67, in an exemplary method of using the bone hook tool 120, the tip end of the bone hook tool 120 is inserted into a hole 133 of a trial part or an implant such as a hip stem 134. A suitable tool 132 (a second tool) such as a blunt trocar 90 is inserted into a hole 135 of a part 136 to be removed (such as a trial neck 110). In some embodiments, the second tool is a blunt trocar, and the part to be removed is a trial neck in a surgical procedure of replacing a hip joint. Meanwhile, the convex such as the round surface of the tool 132 is engaged with the indented surface 124 of the bone hook tool 120. The handle or the arm of the tool 132 is rotated toward in such a way that the tip end of the bone hook tool 120 and the tip of the tool 132 are moved away from each other. The tool 132 is rotated against the indented surface of the bone hook tool 120. The part to be removed is disassembled when the tip of the second tool are moved away from the tip end of the bone hook tool. The part 136 such as a trial neck 110 is then moved out of the hip stem 134. In some embodiments, repeated rotation and movement back and forth may be used to achieve the step of disassembling the part 136 from the hip stem 134. In some embodiments, the bone hook tool 120 having an indented surface 124 can be used to move against or disassemble a ball 138 away from the hip stem 134, as shown in FIG. 68.

(16) Implant Assembly

Figure 69:
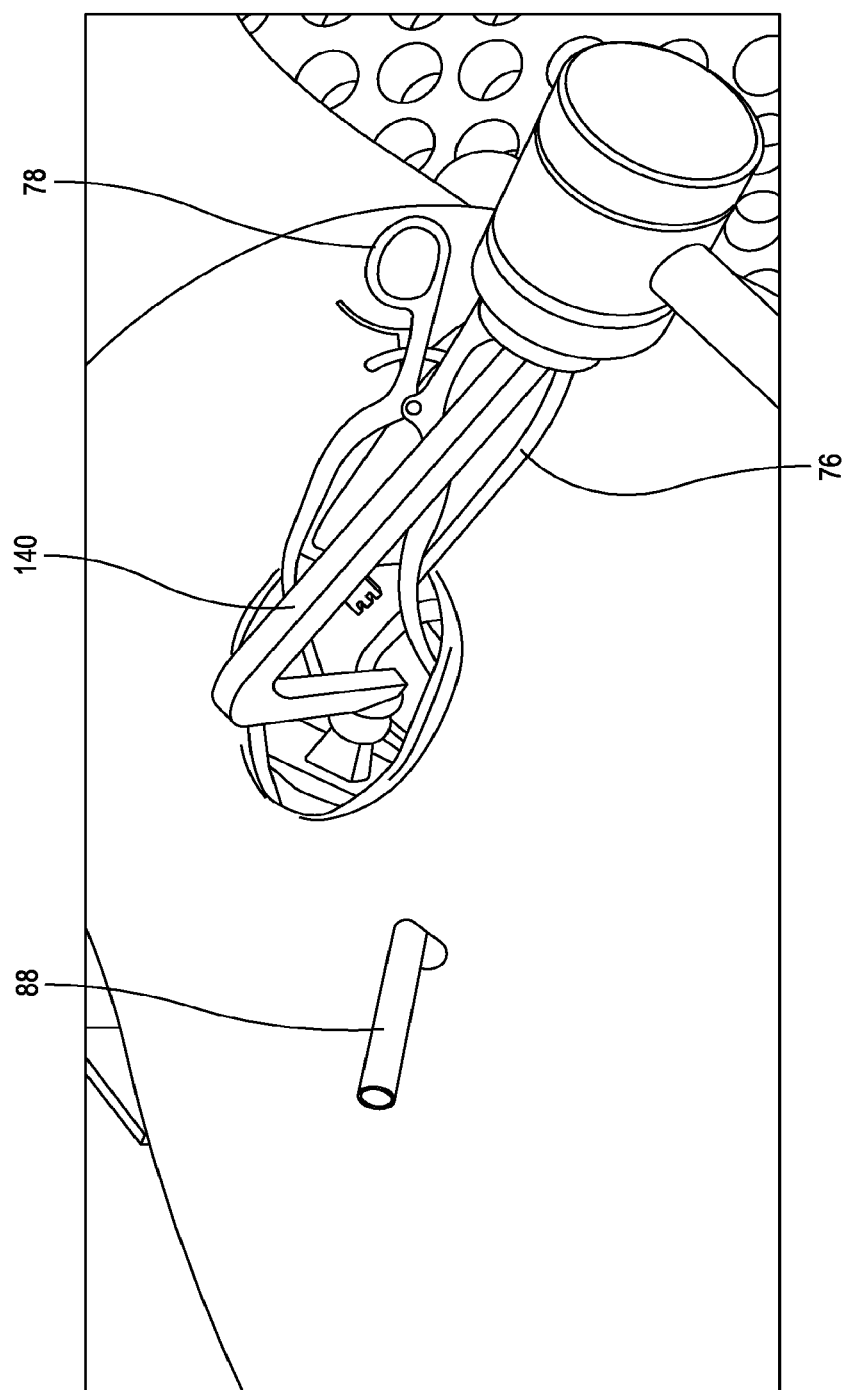
FIGS. 69-70 illustrate a step of assembling implants in some embodiments.
Figure 70:
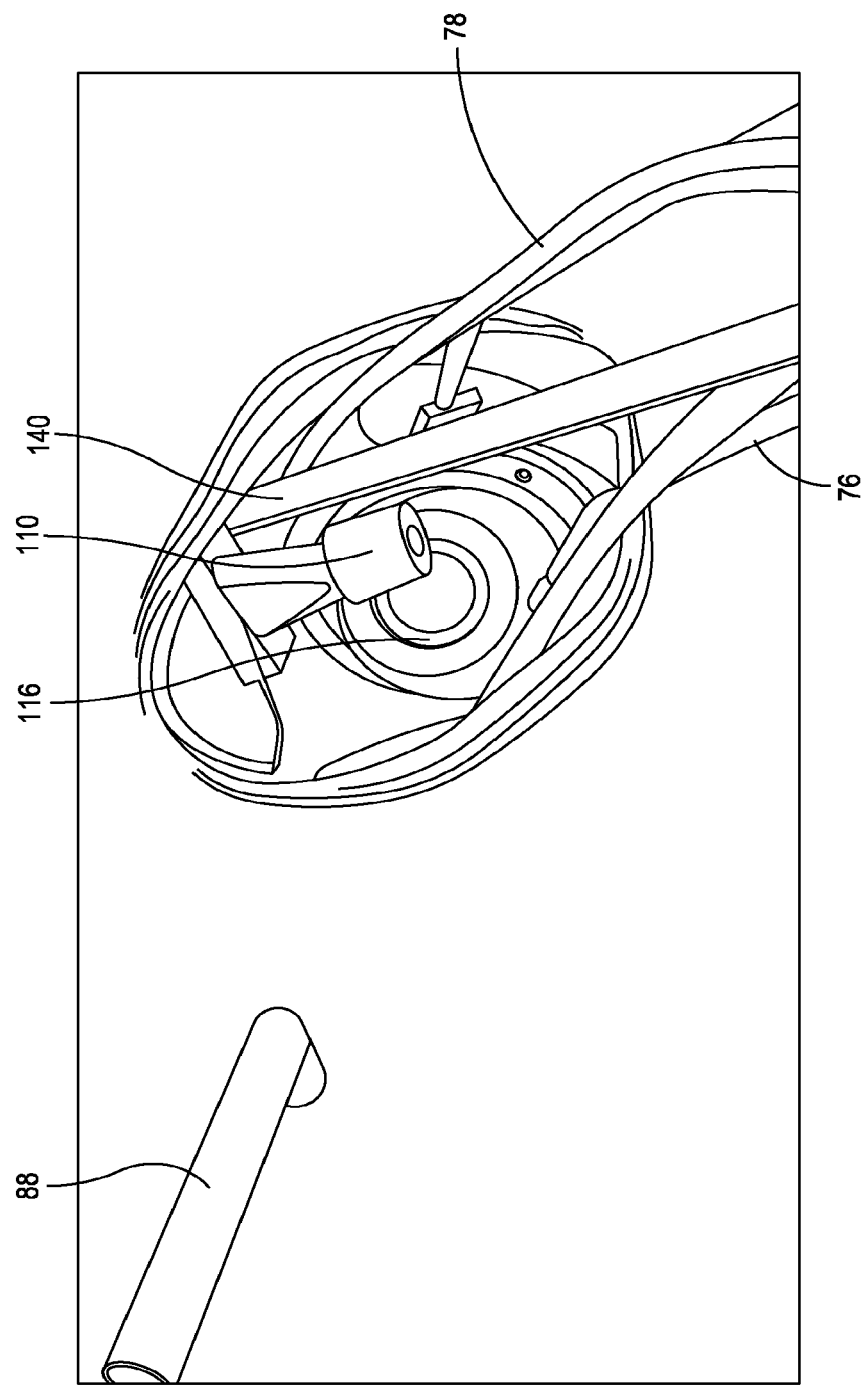

Referring to FIGS. 69-70, a step of assembling implants is performed in some embodiments. After the associated tapers are cleaned and dried, a liner implant of the acetabular cup is then impacted into position using a cup impactor (through the cannula 88) and the appropriate liner impactor (e.g., P/Ns 20070023-20070025). A femoral stem is impacted into position. The depth of the femoral stem from the tip of the greater trochanter can be confirmed using the measurement markings on the end of a canal feeler. The femoral head implant (with neck sleeve if a large femoral head is selected) is placed into the acetabular cup with the opening in a superior-posterior position. In some embodiment, the femoral stem selected is modular, and the modular neck implant is placed into the femoral stem pocket using a set of forceps (e.g., 140) with coated, angled tips to protect the neck taper. In some embodiments, to properly assemble and impact a modular neck, the modular neck and stem pocket tapers need to be clean and dry, and the modular neck can be seated using the offset neck impactor (e.g., P/N 20073009) with three very firm blows from a mallet.

With the tip of the blunt Trocar inserted into the top of the stem, the modular neck is mated into the femoral head after the neck and head tapers are cleaned and dried. As in the trial reduction maneuver, the surgeon controls the leg by pushing and translating the hip under direct visualization through the main incision, while an assistant controls the internal/external rotation of the hip by raising or lowering the foot or knee. Stability of the joint is verified by checking the range of motion, and proper leg length is also confirmed.

(17) Closure

The entire capsule has been preserved, and can be easily re-approximated in-line with the incision. Closure begins by approximating the joint capsule superiorly and inferiorly. If released, the piriformis is reattached to the posterior edge of the gluteus medius. The remainder of the incision is closed in standard fashion.

Although the devices, systems, methods and tools have been described in terms of exemplary embodiments, they are not limited thereto. Rather, the appended claims should be construed broadly, to include other variants and embodiments of the disclosed devices, systems, and methods, which may be made by those skilled in the art without departing from the scope and range of equivalents of the devices, systems, methods and tools.

What is claimed is:

1. A kit comprising:
   a bone hook tool having:
      a lengthwise portion having a trailing handle end and a bent leading end,
      an extension portion extending at an angle from the bent leading end of the lengthwise portion, and
      a bent tip extending from the extension portion, the bent tip having a distal tip end extending back toward the trailing handle end of the lengthwise portion, and the bent tip having an indented surface on an outer side of the bent tip, the indented surface extending across a bend of the bent tip; and
   a second tool having a convex or a rounded surface on a second tool lengthwise portion configured to be placed in the indented surface of the bone hook tool, wherein the second tool is a blunt trocar or other elongate surgical instrument having a conical tip,
   wherein the indented surface of the bone hook tool is configured to accept the convex or the rounded surface of the second tool to remove or disassemble a removable part from a trial part or from an implant without dislocation of a hip in a hip arthroplasty procedure.

2. The kit of claim 1, wherein the indented surface is smooth.

3. The kit of claim 1, wherein the indented surface is textured.

4. The kit of claim 1, wherein a plurality of marks are provided on the indented surface.

5. The kit of claim 1, wherein said removable part is a trial neck in a surgical procedure of replacing a hip joint.

6. The kit of claim 1, wherein the indented surface is configured to accept the rounded surface of the second tool.

7. The kit of claim 1, wherein the bone hook tool is configured to be engaged with the second tool with the distal tip end of the bent tip inserted into a hole on the trial part or the implant and a tip of the second tool inserted into a hole on the removable part, and wherein the second tool is rotated against the indented surface of the bone hook tool.

8. The kit of claim 1, wherein said removable part is disassembled when a tip of the second tool is moved away from the distal tip end of the bone hook tool.

* * * * *